(12) United States Patent
Hayakawa et al.

(10) Patent No.: US 6,365,909 B1
(45) Date of Patent: Apr. 2, 2002

(54) RADIOGRAPHIC IMAGE READING APPARATUS

(75) Inventors: Kazushi Hayakawa; Yoshiyuki Ishimitsu; Takao Tsuda, all of Hino (JP)

(73) Assignee: Konica Corporation, Tokyo (JP)

( * ) Notice: Subject to any disclaimer, the term of this patent is extended or adjusted under 35 U.S.C. 154(b) by 0 days.

(21) Appl. No.: 09/181,480

(22) Filed: Oct. 28, 1998

(30) Foreign Application Priority Data

Nov. 10, 1997 (JP) .............................................. 9-307177
Nov. 21, 1997 (JP) .............................................. 9-321178
Nov. 26, 1997 (JP) .............................................. 9-324407

(51) Int. Cl.$^7$ .............................................. G03B 42/02
(52) U.S. Cl. ........................ 250/584; 250/589; 250/590
(58) Field of Search ................................ 250/584, 589, 250/590

(56) References Cited

U.S. PATENT DOCUMENTS

| 4,814,619 | A | * | 3/1989 | Katsuda et al. ............. 250/589 |
| 4,889,989 | A | * | 12/1989 | Yoshimura et al. ......... 250/589 |
| 4,900,926 | A | | 2/1990 | Yoshimura et al. |
| 5,180,915 | A | | 1/1993 | Ohgoda |
| 5,493,128 | A | * | 2/1996 | Boutet ......................... 250/584 |
| 5,592,374 | A | * | 1/1997 | Fellegara et al. ........... 250/584 |
| 5,675,156 | A | * | 10/1997 | Boeve et al. ................ 250/584 |

FOREIGN PATENT DOCUMENTS

| EP | 0 307 937 | 3/1989 |
| JP | 08-122946 | 5/1996 |
| JP | 09-68765 | 3/1997 |

OTHER PUBLICATIONS

Patent Abstracts of Japan, vol. 097, No. 007, Jul. 31, 1997 & JP 09 068765 A Mar. 11, 1997.

* cited by examiner

Primary Examiner—Constantine Hannaher
Assistant Examiner—Otilia Gabor
(74) Attorney, Agent, or Firm—Frishauf, Holtz, Goodman, Langer & Chick, P.C.

(57) ABSTRACT

An apparatus for reading a radiographic image is provided with a holding section for holding a medium taken out from a cassette, wherein the medium has a recording surface on which the radiographic image is stored, the hold section holding the medium such that the orientation of the recording surface is substantially vertical; and a reading section for reading the radiographic image on the recording surface of the medium held by the holding section, thereby obtaining radiographic image information from the recording surface.

13 Claims, 30 Drawing Sheets

FIG. 20
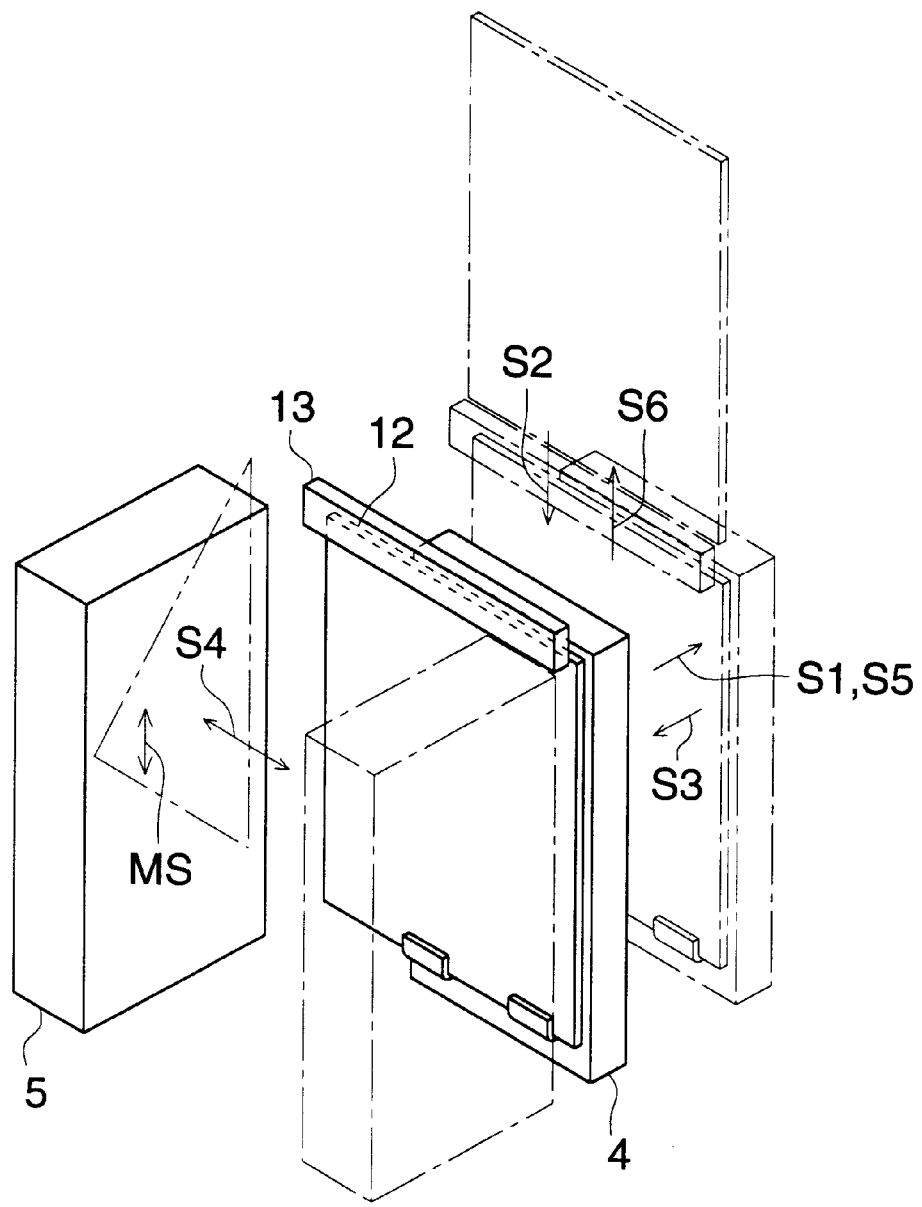
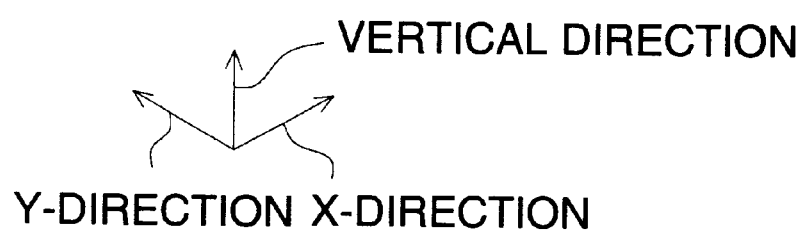

VERTICAL DIRECTION
Y-DIRECTION   X-DIRECTION

FIG. 23
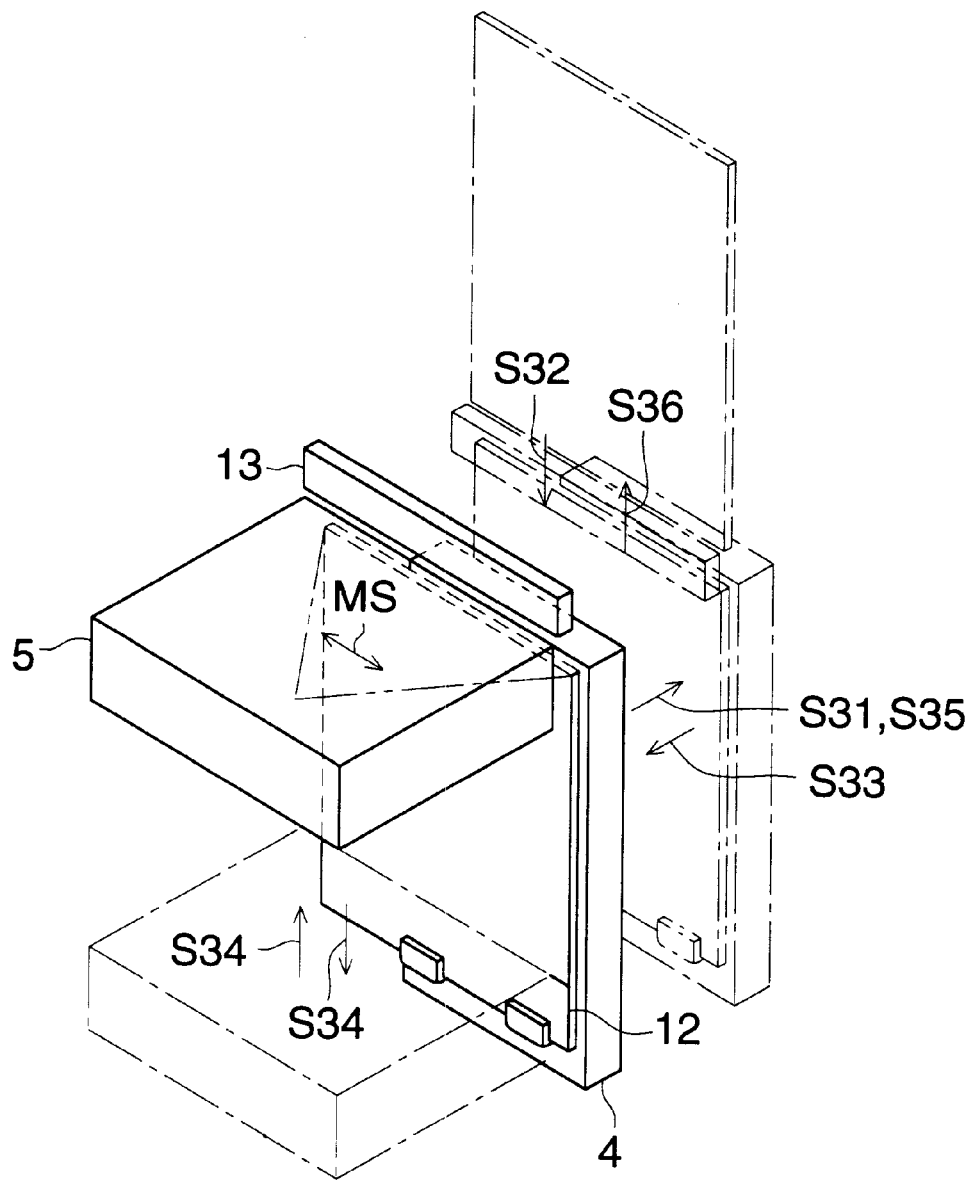
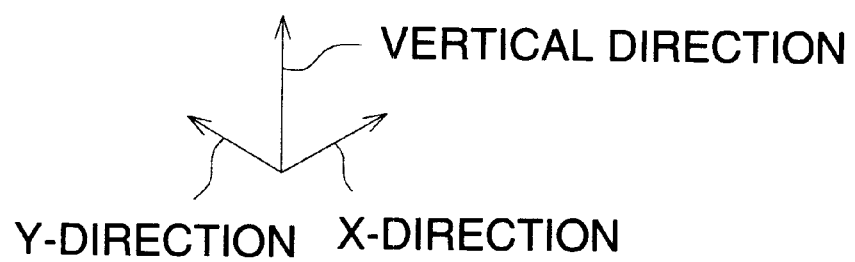

PIROR ART

RADIOGRAPHIC IMAGE READING APPARATUS

BACKGROUND OF THE INVENTION

The present invention relates to a radiographic image reading apparatus wherein a storage phosphor plate is taken out of a cassette containing flat and storage phosphor plates which have been subjected to radiographing, and radiographic images recorded on the storage phosphor plate are read.

TOKKAIHEI No. 9-68765 discloses a radiographic image reading apparatus taking out a storage phosphor sheet from a portable cassette containing storage phosphor sheets which have been subjected to radiographing, and reading radiographic images recorded on the storage phosphor sheet wherein a plurality of cassettes are arranged to be set horizontally, the storage phosphor sheet mentioned above is taken out of any cassette set, and the storage phosphor sheet thus taken out is bent to be conveyed to an image reading section so that radiographic images recorded on the storage phosphor sheet may be read at the image reading section.

Further, TOKKAIHEI No. 8-122946 discloses a technology wherein there are provided a cassette stacker which can accommodate plural sets of cassettes each containing a flat and storage phosphor plate subjected to radiographing so that the storage phosphor plate may be vertical and sends a cassette in succession to the taking out position, a plate holding section which can take out aforesaid storage phosphor plate in the vertical direction from the cassette sent to the taking out position in the cassette stacker and can hold it, and an image reading section which reads radiographic images recorded on the storage phosphor plate through laser scanning, and the plate holding section which is holding the storage phosphor plate is moved in the vertical direction, and the image reading section reads radiographic images recorded on the storage phosphor plate held by the plate holding section.

In the radiographic image reading apparatus described in TOKKAIHEI No. 9-68765, however, it has been difficult to read radiographic images accurately, because the storage phosphor plate is bent to be conveyed and it tends to be damaged accordingly, and the storage phosphor plate has a restriction that it needs to be of a flexible film type.

Further, it has been cleared that the technology described in TOKKAIHEI No. 9-68765 has a problem that a conveyance path forms a curved surface which makes the storage phosphor plate to be jammed easily and makes a loss of expensive storage phosphor plates to be caused easily. In addition, it is difficult to convey the rigid and flat storage phosphor plate along the curved conveyance path from the portable cassette containing the rigid and flat storage phosphor plate. Further, since plural cassettes are set to be stacked vertically in plural steps so that each cassette may be horizontal, a large space for the operations to set cassettes is required in the outskirts of the position of installation, and when a large-sized storage phosphor plate is also made to be capable of being read, a large floor space is required.

On the other hand, the technology described in TOKKAIHEI No. 8-122946 has a problem that it is impossible to take out a storage phosphor plate from the cassette and to read radiographic images recorded on the storage phosphor plate until the cassette is sent to the taking out position, and interruption processing can not be conducted. Further problem is that the apparatus is of a complicated structure and expensive, which is caused by the mechanism wherein the cassette stacker sends plural cassettes set simultaneously and intermittently and thereby sends plural cassettes to the taking out position in succession.

An object of the invention is to make it unnecessary to bend the storage phosphor plate to convey it, and to make the floor space of the apparatus small, which are resulted from consideration of the problems stated above.

An object of the invention is to make the space in the outskirts of the installation position in the horizontal direction unnecessary while making interruption processing possible without providing a conveyance path having the curved surface which easily causes jam of the storage phosphor plate, and to make the cassette stacker to be of a simple structure and to be inexpensive, while avoiding a large floor space even when a large-sized storage phosphor plate is made to be capable of being read.

Further object of the invention is to make the structure of a cassette stacker simple and to make the cassette stacker inexpensive while making interruption processing possible without providing a conveyance path having the curved surface which easily causes jam of the storage phosphor plate, and to make stable and accurate image reading for a long time to be easy.

Another object is to avoid a large floor space in the case where plural cassettes can be set, the storage phosphor plate can be taken out from any cassette set, and radiographic images recorded on the storage phosphor plate can be read, and further to shorten the total time necessary for reading radiographic images recorded on the storage phosphor plate.

FIG. 30 is a structural perspective view of a radiographic image reading apparatus in the prior art.

In the drawing, on the upper part of the apparatus, there is provided cassette stacker section 1001 on which a plurality of cassettes 1002 each having therein a rigid medium having thereon accumulated radiographic images are set.

Inside the lower portion of the apparatus, there are provided an image reading section which reads radiographic images on the medium and a medium conveyance section which takes a medium out of the cassette positioned at extracting position A of cassette stacker section 1002, then conveys it to an image reading section, and returns the medium finished in terms of reading to cassette 1002 positioned at the extracting position A.

Cassette stacker section 1001 is arranged to drive cassette 1002 which is set to slide it in the direction of arrow B in the drawing so that the cassette 1002 containing the medium to be read may be positioned at the extracting position A.

In the radiographic image reading apparatus having the aforesaid structure, however, when the cassette stacker section 1001 to be driven to slide in the direction of arrow B is exposed from the apparatus, there is a fear that a part of the human body is drawn in a gap of cassettes 1002 set when the cassette stacker section 1001 slides.

It is therefore necessary to provide a cover which covers the cassette stacker section 1001.

However, when this cover is provided, operations to open and close the cover are necessary when setting cassette 1002 on the cassette stacker section 1001, or when taking the cassette 1002 out of the cassette stacker section 1001, which worsens an operation.

With reference to FIG. 31 showing a front structural diagram and FIG. 32 showing a right side structural diagram in FIG. 31, an overall structure of a conventional radiographic image recording/reading apparatus will be explained.

In these drawings, the numeral 1001 represents a the cassette stacker section 1001 in which three racks 1012, 1013 and 1014 are formed vertically, and cassettes 1002, 1003 and 1004 each having therein a medium on which radiographic images are accumulated are respectively set on the racks 1012, 1013 and 1014.

Incidentally, the cassette stacker section 1001 is arranged so that cassettes 1002, 1003 and 1004 which are different each other in terms of size can be set as shown in the drawing.

On the lower portion of the cassette stacker section 1001, there is provided image reading section 1005 which reads radiographic images on a medium in each of cassettes 1002, 1003 and 1004. Further, between the cassette stacker section 1001 and the image reading section 1005, there is provided medium conveyance section 1006 which takes a medium out of either cassette among set cassettes 1002, 1003 and 1004, then conveys it to image reading section 1005 and conveys the medium finished in terms of reading to the cassette.

On the upper portion of the cassette stacker section 1001, there are arranged operation section 1007 through which ON/OFF for the apparatus, selection of cassettes and various image processing are conducted, and display section 1008 which displays radiographic images read by image reading section 1005 and the state of the apparatus.

As shown in FIG. 33 displaying a structural diagram representing a cassette stacker section in FIG. 31 viewed from the upper part, each of cassettes 1002, 1003 and 1004 set respectively on the racks 1012, 1013 and 1014 of the cassette stacker section 1001 is set to be in contact with plane A which is an inner plane for the racks 1012, 1013 and 1014 in the drawing and side B which is a right hand side for the racks 1012, 1013 and 1014.

On the central portion on the front of the cassette stacker section 1001, there is formed a cutout 1010 which makes it easy to take out a small-sized cassette, namely, cassettes 1003 and 1004 in the present conventional example.

However, the radiographic image recording/reading apparatus stated above has following problems.

(1) Since the operation section 1007 and the display section 1008 are provided on the upper portion of the cassette stacker section 1001, it is required to turn eyes upon the upper portion after setting cassettes 1002, 1003 and 1004 on the cassette stacker section 1001 to operate on the operation section 1007, or to confirm images on the display section 1008, which represents a poor operation.

(2) Cassettes 1002, 1003 and 1004 are to be set so that they may be set with the inner side of the apparatus serving as a reference side, namely, they come in contact with inner plane A of racks 1012, 1013 and 1014.

Therefore, as shown in FIG. 32, when setting small-sized cassette 1003 on rack 1013 located between rack 1012 and rack 1014 on which large-sized cassettes 1002 and 1004 are respectively set, or when taking out small-sized cassette 1003 set on rack 1013, it is inconvenient to operate.

The invention has been achieved in view of the problems stated above, and its object is to provide a radiographic image recording/reading apparatus allowing easy operations.

SUMMARY OF THE INVENTION

The above objects are attained by a radiographic image reading apparatus having the following structures.

An apparatus for reading a radiographic image, has
a holding section for holding a medium taken out from a cassette, wherein the medium has a recording surface on which the radiographic image is stored, the hold section holding the medium such that the orientation of the recording surface is substantially vertical; and
a reading section for reading radiographic image on the recording surface of the medium held by the holding section, thereby obtaining radiographic image information from the recording surface.

The above apparatus, further has a stacker on which the cassette is placed, wherein the holding section takes the medium out from the cassette placed on the stacker.

The above apparatus, further has a display section provided close to the stacker in a substantially horizontal direction and for displaying the radiographic image information.

Furthermore, the above objects can be attained by a radiographic image reading apparatus having the following preferable structures.

(1) A radiographic image reading apparatus having therein a cassette setting section capable of setting a portable cassette containing a flat and storage phosphor plate subjected to radiographing so that a plane of the storage phosphor plate may be almost in parallel with the vertical direction, and an apparatus main body which takes the storage phosphor plate out of the cassette set at the cassette setting section, and reads radiographic images recorded on the storage phosphor plate while a plane of the storage phosphor plate thus taken out is almost in parallel with the vertical direction.

Due to the invention described in Item 1, it is not necessary to bend the storage phosphor plate to convey it, and a floor space for the apparatus can be small, because radiographic images recorded on the storage phosphor plate are read while the storage phosphor plate taken out is left to be in the vertical direction.

(2) The radiographic image reading apparatus described in Item 1, wherein a cassette is set on the cassette setting section so that the longitudinal direction of the storage phosphor plate may be in the vertical direction, and the apparatus main body reads radiographic images recorded on the storage phosphor plate by making a laser beam to scan almost in the horizontal direction while moving the storage phosphor plate in the direction which is almost vertical.

Due to the invention described in Item 2, a floor space for the apparatus can be small because the longitudinal direction of the storage phosphor plate is in the vertical direction, the scanning direction of the laser beam is in the lateral direction of the storage phosphor plate because the scanning direction of the laser beam is almost in the horizontal direction, and the deflecting angle of the laser beam is small and difference of image quality between the central portion and peripheral portion on the image plane is small, whereby it is possible to properly read radiographic images recorded on the storage phosphor plate.

(3) The radiographic image reading apparatus described in Item 2, wherein the apparatus main body reads radiographic images recorded on the storage phosphor plate by making the laser beam to scan almost in the horizontal direction while taking out almost in the vertical direction the storage phosphor plate from the cassette that is set on the cassette setting section.

Due to the invention described in Item 3, it is possible to read quickly radiographic images recorded on the storage phosphor plate.

(4) The radiographic image reading apparatus described in Item 1 or Item 2, wherein the apparatus main body reads radiographic images recorded on the apparatus main body reads radiographic images recorded on the storage phosphor plate by making the laser beam to scan almost in the horizontal direction while loading the storage phosphor plate almost in the vertical direction in the cassette set on the cassette setting section.

Due to the invention described in Item 4, it is possible to load quickly in the cassette the storage phosphor plate on which the radiographic images recorded thereon have been read.

(5) A radiographic image reading apparatus to take out a storage phosphor plate from a portable cassette containing a flat and storage phosphor plate subjected to radiographing and to read radiographic images recorded on the storage phosphor plate, wherein there are provided, when a certain direction in the horizontal plane is called an X-direction, a cassette stacker in which plural cassettes can be set side by side so that the storage phosphor plates may be almost perpendicular to the X-direction and different each other in terms of position in the X-direction, a plate holding section which, due to its capability to move at least in the X-direction, can take out the storage phosphor plate almost in the vertical direction from any cassette set in the cassette stacker and hold it, and an image reading section which reads radiographic images recorded on the storage phosphor plate that is held by the plate holding section.

In the invention described in Item 1, the cassette stacker is one wherein plural cassettes can be set side by side so that the storage phosphor plates may be almost perpendicular to the X-direction and different each other in terms of position in the X-direction, and a plate holding section is one which, due to its capability to move at least in the X-direction, can take out the storage phosphor plate almost in the vertical direction from any cassette set in the cassette stacker and hold it. Therefore, a large floor space is not required even when arranging so that a storage phosphor plate having a large area can also be read, and a large space for the operation to set a cassette in the vicinity of the installation position in the horizontal direction is not required, and it is further possible to make the structure of the cassette stacker and plate holding section simple and to make them to be inexpensive. Further, since the image reading section reads radiographic images recorded on the storage phosphor plate that is held by the plate holding section. It is possible to conduct interruption processing wherein a storage phosphor plate is taken out of the cassette set newly and images are read from the storage phosphor plate, even when some cassettes not yet read are already set under the condition that a conveyance path having a curved surface which easily causes a jam of the storage phosphor plate is not provided.

(6) The radiographic image reading apparatus described in Item 5, wherein the image reading section is one to read radiographic images recorded on the storage phosphor plate by causing a laser beam to scan in the direction that is almost perpendicular to the X-direction, and the image reading section reads radiographic images recorded on the storage phosphor plate after the plate holding section holding the storage phosphor plate and the image reading section are moved relatively at least in the X-direction and are set at the prescribed relative positions in the X-direction.

The invention described in Item 6 make it easy to set at the prescribed relative position required by laser scanning.

(7) A radiographic image reading apparatus to take out a storage phosphor plate from a portable cassette containing a flat and storage phosphor plate subjected to radiographing and to read radiographic images recorded on the storage phosphor plate, wherein there are provided, when a certain direction in the horizontal plane is called an X-direction, a cassette stacker in which plural cassettes can be set, a plate holding section which, due to its capability to move at least in the X-direction, can take out the storage phosphor plate from any cassette set in the cassette stacker and hold it, and an image reading section which reads radiographic images recorded on the storage phosphor plate that is held by the plate holding section, by causing a laser beam to scan in the direction that is almost perpendicular to the X-direction, and the image reading section reads radiographic images recorded on the storage phosphor plate after the plate holding section holding the storage phosphor plate is moved at least in the X-direction and is set at the prescribed positions in the X-direction.

In the invention described in Item 7, the cassette stacker is one wherein plural cassettes can be set side by side, and the plate holding section is one which, due to its capability to move at least in the X-direction, can take out the storage phosphor plate from any cassette set in the cassette stacker and hold it. Therefore, it is possible to make the structure of the cassette stacker simple and to make it to be inexpensive. Further, since radiographic images recorded on the storage phosphor plate that is held by the plate holding section are read after the plate holding section holding the storage phosphor plate is moved in the X-direction and is set at the prescribed position in the X-direction, it is possible to take out a storage phosphor plate from the cassette set newly and to conduct interruption processing for reading images from the storage phosphor plate, even when some cassettes not yet read are already set under the condition that a conveyance path having a curved surface which easily causes a jam of the storage phosphor plate is not provided. Further, since the image reading section is fixed in the X-direction, it is easy to arrange so that accurate image reading can be conducted stably for a long time.

Since the plate holding section takes the storage phosphor plate out of the cassette set in the cassette stacker and holds it, it is possible to use a moving mechanism for moving at least in the X-direction and a moving mechanism for moving at least in the X-direction for holding the storage phosphor plate for an image reading section fixed in the X-direction to read radiographic images and for setting it at the prescribed position in the X-direction in common. Due to this, it is possible to make the structure simple.

(8) A radiographic image reading apparatus to take a storage phosphor plate from a portable cassette containing a flat and storage phosphor plate subjected to radiographing and to read radiographic images recorded on the storage phosphor plate, wherein there are provided, when a certain direction in the horizontal plane is called an X-direction, a cassette stacker in which plural cassettes can be set side by side so that the storage phosphor plates may be almost perpendicular to the X-direction and different each other in terms of position in the X-direction, a plate holding section which, due to its capability to move at least in the X-direction, can take out the storage phosphor plate from any cassette set in the cassette stacker and hold it, and an image reading section which reads, through laser scanning, radiographic images recorded on the storage phosphor plate that is held by the plate holding section, by causing a laser beam to scan in the direction which is almost perpendicular to the X-direction. and the image reading section reads radiographic images recorded on the storage phosphor plate after the image reading section is moved at least in the X-direction and is set at the prescribed relative position in the X-position against the plate holding section.

In the invention described in Item 8, a cassette stacker is one in which plural cassettes can be set side by side so that the storage phosphor plates may be almost perpendicular to the X-direction and different each other in terms of position in the X-direction, and a plate holding section, due to its capability to move at least in the X-direction, can take out the storage phosphor plate from any cassette set in the cassette stacker and hold it, a large floor space is not required even when arranging so that a storage phosphor plate having a large area can also be read, and the cassette stacker can be made simple in terms of structure and inexpensive in terms of cost. Further, since the reading section is one wherein it reads radiographic images recorded on the storage phosphor plate held by the plate holding section, after the image reading section is moved in the X-direction and then is set at the prescribed relative position in the X-direction against the plate holding section, it is possible to shorten the total time required for reading radiographic images recorded on one storage phosphor plate by moving the image reading section in the X-direction while the plate holding section is taking out the storage phosphor plate.

(9) The radiographic image reading apparatus described in either one of Item 5–Item 9, wherein the plate holding section loads the storage phosphor plate holding radiographic images obtained through reading by the image reading section in either cassette set in the cassette stacker.

Due to the invention described in Item 9, it is possible to take out a storage phosphor plate from any cassette set in the cassette stacker by means of one plate holding section, and to load the storage phosphor plate in either cassette set in the cassette stacker, which makes the structure simple.

(10) A radiographic image reading apparatus equipped with a cassette stacker section which is protruded from an apparatus and has therein plural cassettes each containing a rigid medium on which radiographic images are accumulated, an image reading section provided inside an apparatus, and with a medium conveyance section which is provided inside an apparatus, and takes out a medium from a cassette set in the cassette stacker section, then conveys it to the image reading section, and sends the medium which has been read back to the cassette stacker section, wherein the medium conveyance section moves to the aimed cassette out of plural cassettes set in the cassette stacker, then engages with a longer side of the medium in the cassette, then moves in the direction of the shorter side of the medium, and takes the medium out of the cassette.

Since the medium conveyance section provided inside an apparatus moves to the aimed cassette in the cassette stacker section and takes out the medium in the cassette, a movable portion is not exposed to be out of the apparatus. Therefore, an enclosure to cover the movable portion is not required, resulting in easy operation.

When taking out a medium from a cassette, the medium is taken out in the direction of its shorter side, which leads to reduction of the time to take out.

Further, the medium conveyance section can convey the medium stably by engaging with the longer side of the medium.

(11) The cassette mentioned above is set in the aforesaid cassette stacker section with its longer side extending almost horizontally.

The cassette is set in the cassette stacker section with its longer side extending almost horizontally, namely, with its shorter side being almost vertical, which can make the height of the cassette stacker section low.

(12) The image reading section stated above is composed of a main scanning section which conducts main scanning on the medium in the direction of its shorter side, and of a sub-scanning mechanism driving section which drives the aforesaid main scanning section in the direction of the longer side of the medium.

Since the main scanning section scans the medium in its shorter side direction, it is possible to make a scanning optical system small, which leads to a small-sized apparatus and a low cost thereof.

(13) A ball screw is used in the sub-scanning mechanism driving section stated above.

Employment of the ball screw which is less resistant reduces speed unevenness in the sub-scanning direction, and makes it possible to obtain excellent images.

(14) A linear motor is used in the sub-scanning mechanism driving section.

Employment of the linear motor makes the mechanism to convert rotary motion into linear motion to be unnecessary, which leads to cost reduction.

(15) A radiographic image recording/reading apparatus having therein a cassette stacker section in which a cassette containing a medium having thereon accumulated radiographic images is set, an image reading section which reads the radiographic images on the medium, a medium conveyance section which takes out a medium from the cassette set in the cassette stacker section, then conveys the medium to the image reading section, and sends the medium which has been read through back to the cassette stacker section, and a display section which displays images obtained through reading by the image reading section, wherein the display section and the cassette stacker section are arranged side by side in the direction which is almost horizontal.

Owing to the display section and the cassette stacker section arranged side by side in the direction which is almost horizontal, when confirming images on the display section after setting a cassette in the cassette stacker section, less movement of eyes is required, which leads to easy operation.

(16) A touch panel is provided on a display screen of the display section.

Owing to the touch panel provided on the display screen of the display section, operations for an apparatus can be done on the display screen. Therefore, when operating the apparatus after setting a cassette in the cassette stacker section, less movement of eyes is required, which leads to easy operation.

(17) The touch panel stated above is of an optical system wherein it responds to interception of light.

Compared with a resistive film system and an analog capacity coupling system which require a film provided on the display screen, no film is required and transmittance on the display screen is excellent accordingly.

(18) A cassette to be set in the cassette stacker section is set with this side of the apparatus serving as a reference side.

Owing to the cassette which is set with a reference of this side of the apparatus, it is easy to set and take out a small-sized cassette, which leads to easy operation.

(Explanation of terminology)

Herein, the medium is a medium capable of storing radioactive rays having passed through an object. The medium can stores the radioactive rays at least for a moment. The medium is a medium containing a semiconductor detector, a stimulative phosphour and so on and is an intermediate medium from which the radiographic image is converted into electric signals.

A reading surface of a medium is a surface adapted to face the reading section.

A storage phosphor plate is a plate having a layer of a storage phosphor. It is preferable that the storage phosphor plate is a flat plate which is highly rigid. It is preferable, in particular, that a base board of the plate is of a material such as a metal, ceramic and fiber reinforced resin. The storage phosphor is one which accumulates energy based on radiation transmissivity distribution of a subject for a dose of radiation irradiated from a radiation generating source, and forms a latent image. A preferable storage phosphor is a stimulating phosphor.

It is preferable that the storage phosphor plate is one wherein a layer of a storage phosphor is provided on a support through gas phase sedimentation or coating. The layer of a storage phosphor is preferably shielded or covered by a protection member to avoid an environmental harmful influence or damage.

In the present invention, a cassette means a portable cassette containing therein a flat and storage phosphor plate subjected to radiographing. In the present invention, a cassette setting section is one wherein cassettes can be set so that planes of storage phosphor plates may be almost in parallel with each other in the vertical direction.

Further, in the present invention, the apparatus main body is one which takes out the storage phosphor plate almost in the vertical direction from the cassette set in the cassette setting section, and reads radiographic images recorded on the storage phosphor plate while the storage phosphor plate is kept to be almost vertical.

It is preferable from the viewpoint of various aspects such as simple structures and small-sized apparatuses that planes of the storage phosphor plates contained respectively in plural cassettes set in the cassette setting section are almost in parallel with each other. In this case, it is preferable that there is provided a plate holding section which can hold the storage phosphor plate which is taken out of the cassette set in the cassette setting section. It is preferable that the plate holding section can take out to hold the storage phosphor plate contained in the cassette from any cassette which is set, by moving at least in the direction that is perpendicular to the plane of the storage phosphor plate, and can load in any cassette that is set the storage phosphor plate which the plate holding section is holding.

In the invention, the X-direction is one direction in the horizontal plane, while Y-direction is a direction perpendicular to the X-direction in the horizontal plane, and an angle between the X-direction and the Y-direction, an angle between the vertical direction and the X-direction and an angle between the vertical direction and the Y-direction all represent a right angle.

With regard to a relative movement at least in the X-direction between the image reading section and the plate holding section, a movement of the image reading section at least in the X-direction, and a movement of the plate holding section at least in the X-direction, a movement having moving components in the X-direction is enough, and a diagonal movement upwards having moving components in the X-direction and a diagonal movement downwards having moving components in the X-direction, for example, are also acceptable.

Though the image reading section is preferably fixed, it may also be of a type wherein the image reading section moves. In addition, though the image reading section is preferably one wherein radiographic images recorded on the storage phosphor plate are read through laser scanning, it may also be of a type wherein radiographic images recorded on the storage phosphor plate are read through another method.

As a type to read radiographic images recorded on the storage phosphor plate through laser scanning, there are given a type wherein main scanning by a laser beam is conducted in the vertical direction and sub-scanning is conducted by moving an image reading section and a storage phosphor plate relatively in the horizontal direction which is in parallel with a plane of the storage phosphor plate, and a type wherein main scanning by a laser beam is conducted in the horizontal direction which is in parallel with a plane of the storage phosphor plate, and sub-scanning is conducted by moving an image reading section and a storage phosphor plate relatively in the vertical direction, to which the invention is not limited.

In the type wherein main scanning by means of a laser beam is conducted in the vertical direction and sub-scanning is conducted by moving an image reading section and a storage phosphor plate relatively in the horizontal direction that is in parallel with a plane of the storage phosphor plate, movement accompanied by load of gravity is not required. Therefore, stable sub-scanning can be conducted, and it is easy to make images read to be excellent, which is preferable. As a type to conduct sub-scanning by moving an image reading section and a storage phosphor plate relatively in the horizontal direction (hereinafter referred to as Y-direction) that is in parallel with a plane of the storage phosphor plate, there are given a type (shown also in an embodiment) wherein sub-scanning is conducted by fixing plate holding section 4 and moving image reading section 5 in the Y-direction as shown in FIG. 20, and a type wherein sub-scanning is conducted by fixing image reading section 5 and moving plate holding section 4 which holds storage phosphor plate 12 in the Y-direction as shown in FIG. 21, to which the invention is not limited.

As a type to conduct main scanning in the Y-direction by means of a laser beam and to conduct sub-scanning by moving an image reading section and a storage phosphor plate relatively in the vertical direction, there are given a type wherein sub-scanning is conducted by fixing image reading section 5 and by moving storage phosphor plate 12 held by plate holding section 4 in the vertical direction as shown in FIG. 22, and a type wherein sub-scanning is conducted by fixing plate holding section 4 holding a storage phosphor plate and by moving image reading section 5 in the vertical direction as shown in FIG. 23, to which the invention is not limited.

Now, types shown in FIG. 20–FIG. 23 will be explained.

In the type (shown also in an embodiment) wherein sub-scanning is conducted by fixing plate holding section 4 and by moving image reading section 5 in the Y-direction as shown in FIG. 20, the image reading section 5 conducts main scanning MS by means of a laser beam in the vertical direction, and to begin with, in the first place (S1), plate holding section 4 moves at least in the X-direction and stops at the prescribed take-out position in the X-direction, and in the second place (S2), the plate holding section 4 takes out storage phosphor plate 12 at the prescribed take-out position in the X-direction and holds it, then, in the third place (S3), the plate holding section 4 moves at least in the X-direction and stops at the prescribed take-out position in the X-direction, and in the fourth place (S4), image reading section 5 moves in the Y-direction and thereby conducts sub-scanning on the storage phosphor plate 12 when the plate holding section 4 holding the storage phosphor plate 12 is fixed, then, n the fifth place (S5), the plate holding section 4 moves at least in the X-direction and stops at the prescribed loading position in the X-direction, and in the sixth place (S6), the plate holding section 4 makes erasing section 13 to erase residual images remaining on the storage phosphor plate 12 while loading the storage phosphor plate 12 in the cassette at the prescribed loading position in the X-direction.

In the type wherein sub-scanning is conducted by fixing image reading section 5 and by moving plate holding section 4 in the Y-direction as shown in FIG. 21, the image reading section 5 is one to conduct main scanning MS by means of a laser beam in the vertical direction, and is fixed, and to begin with, in the first place (S11), plate holding section 4 moves at least in the X-direction and stops at the prescribed take-out position in the X-direction, and in the second place (S12), the plate holding section 4 takes out storage phosphor plate 12 at the prescribed take-out position in the X-direction and holds it, then, in the third place (S13), the plate holding section 4 moves at least in the X-direction and stops at the prescribed take-out position in the X-direction, and in the fourth place (S14), the plate holding section 4 holding storage phosphor plate 12 moves in the Y-direction while keeping the reading position in the X-direction and conducts sub-scanning on the storage phosphor plate 12, then, in the fifth place (S15), the plate holding section 4 holding the storage phosphor plate 12 moves in the Y-direction and thereby returns to the original position in the Y-direction, in the sixth place (S16), the plate holding section 4 moves at least in the X-direction and stops at the prescribed loading position in the X-direction, and in the seventh place (S17), the plate holding section 4 makes erasing section 13 to erase residual images remaining on the storage phosphor plate 12 while loading the storage phosphor plate 12 in the cassette at the prescribed loading position in the X-direction.

In the type wherein sub-scanning is conducted by fixing image reading section 5 and by moving storage phosphor plate 12 held by the plate holding section 4 in the vertical direction as shown in FIG. 22, the image reading section 5 is one to conduct main scanning MS by means of a laser beam in the Y-direction, and is fixed, and to begin with, in the first place (S21), plate holding section 4 moves at least in the X-direction and stops at the prescribed take-out position in the X-direction, and in the second place (S22), the plate holding section 4 takes out storage phosphor plate 12 at the prescribed take-out position in the X-direction and holds it, then, in the third place (S23), the plate holding section 4 moves at least in the X-direction and stops at the prescribed take-out position in the X-direction, and in the fourth place (S24), the storage phosphor plate 12 is subjected to sub-scanning when the plate holding section 4 holding storage phosphor plate 12 moves the storage phosphor plate 12 in the vertical direction while the plate holding section 4 is fixed, then, in the fifth place (S25), the plate holding section 4 holding the storage phosphor plate 12 returns the storage phosphor plate 12 to the original position in the vertical direction, in the sixth place (S26), the plate holding section 4 moves at least in the X-direction and stops at the prescribed loading position in the X-direction, and in the seventh place (S27), the plate holding section 4 makes erasing section 13 to erase residual images remaining on the storage phosphor plate 12 while loading the storage phosphor plate 12 in the cassette at the prescribed loading position in the X-direction.

In the type wherein sub-scanning is conducted by fixing plate holding section 4 holding storage phosphor plate 12 and by moving image reading section 5 in the vertical direction as shown in FIG. 23, the image reading section 5 conducts main scanning MS by means of a laser beam in the Y-direction, and to begin with, in the first place (S31), plate holding section 4 moves at least in the X-direction and stops at the prescribed take-out position in the X-direction, and in the second place (S32), the plate holding section 4 takes out storage phosphor plate 12 at the prescribed take-out position in the X-direction and holds it, then, in the third place (S33), the plate holding section 4 moves at least in the X-direction and stops at the prescribed take-out position in the X-direction, and in the fourth place (S34), the image reading section 5 conducts sub-scanning on the storage phosphor plate 12 by moving in the vertical direction when the plate holding section 4 holding the storage phosphor plate 12 is fixed, then, in the fifth place (S35), the plate holding section 4 moves at least in the X-direction and stops at the prescribed loading position in the X-direction, and in the sixth place (S36), the plate holding section 4 makes erasing section 13 to erase residual images remaining on the storage phosphor plate 12 while loading the storage phosphor plate 12 in the cassette at the prescribed loading position in the X-direction.

Incidentally, in the examples stated above, all cassette stackers are represented by one wherein plural portable cassettes each containing a flat and storage phosphor plate subjected to radiographing can be set side by side so that a plane of the storage phosphor plate contained may be vertical, and a plate holding section can take out the storage phosphor plate contained in the cassette from any cassette set in the cassette stacker in the vertical direction by moving in the direction (hereinafter referred to as X-direction) perpendicular to the plane of the storage phosphor plate, and can hold the storage phosphor plate, and it can further load the storage phosphor plate which is held in any cassette set in the cassette stacker by moving the storage phosphor plate in the vertical direction. However, the invention is not limited to the foregoing, and the type shown below, for example, is included in the invention, or the type to move obliquely or other types are included in the invention.

For example, the type mentioned above may be one wherein plural portable cassettes each containing a flat and storage phosphor plate subjected to radiographing can be set side by side so that a plane of the storage phosphor plate contained may be vertical, and a plate holding section can take out the storage phosphor plate contained in the cassette from any cassette set in the cassette stacker in the Y-direction by moving in the X-direction and can hold the storage phosphor plate, and it can further load the storage phosphor plate which is held in any cassette set in the cassette stacker by moving the storage phosphor plate in the Y-direction, as shown in FIG. 24, and image reading section 5 is one to conduct main scanning MS by means of a laser beam in the Y-direction, and to begin with, in the first place (S51), plate holding section 4 moves at least in the X-direction and stops at the prescribed take-out position in the X-direction, and in the second place (S52), the plate holding section 4 takes out storage phosphor plate 12 in the Y-direction at the prescribed take-out position in the X-direction and holds it, in the third place (S53), the plate holding section 4 moves at least in the X-direction and stops at the prescribed reading position in the X-direction, and in the fourth place (S54), the image reading section 5 conducts sub-scanning on the storage phosphor plate 12 by moving in the vertical direction when the plate holding section 4 holding the storage phosphor plate 12 is fixed, then, in the fifth place (S55), the plate holding section 4 moves at least in the X-direction and stops at the prescribed loading position in the X-direction, and in the sixth place (S56), the plate holding section 4 makes erasing section 13 to erase residual images remaining on the storage phosphor plate 12 while loading the storage phosphor plate 12 in the cassette by moving it in the Y-direction at the prescribed loading position in the X-direction.

The type mentioned above may further be one, for example, wherein plural portable cassettes each containing a flat and storage phosphor plate subjected to radiographing can be set side by side so that a plane of the storage phosphor plate contained may be in the horizontal plane, and a plate holding section can take out the storage phosphor plate contained in the cassette from any cassette set in the cassette stacker in the Y-direction by moving in the vertical direction and can hold the storage phosphor plate, and it can further load the storage phosphor plate which is held in any cassette set in the cassette stacker by moving the storage phosphor plate in the Y-direction, as shown in FIG. 25, and image reading section 5 is one to conduct main scanning MS by means of a laser beam in the Y-direction, and to begin with, in the first place (S61), plate holding section 4 moves at least in the vertical direction and stops at the prescribed take-out position in the vertical direction, and in the second place (S62), the plate holding section 4 takes out storage phosphor plate 12 in the Y-direction at the prescribed take-out position in the vertical direction and holds it, in the third place (S63), the plate holding section 4 moves at least in the vertical direction and stops at the prescribed reading position in the vertical direction, and in the fourth place (S64), the image reading section 5 conducts sub-scanning on the storage phosphor plate 12 by moving in the X-direction when the plate holding section 4 holding the storage phosphor plate 12 is fixed, then, in the fifth place (S65), the plate holding section 4 moves at least in the vertical direction and stops at the prescribed loading position in the vertical direction, and in the sixth place (S66), the plate holding section 4 makes erasing section 13 to erase residual images remaining on the storage phosphor plate 12 while loading the storage phosphor plate 12 in the cassette by moving it in the Y-direction at the prescribed loading position in the vertical direction.

In the invention, the erasing section is one to erase residual images remaining on a storage phosphor plate when loading the storage phosphor plate from which the radiographic images have been read at the image reading section into the cassette set in the cassette stacker, and the erasing section which is provided on the plate holding section is preferable. The type wherein the erasing section is provided on the plate holding section includes either a type wherein the erasing section is fixed on the plate holding section, or a type wherein the erasing section is provided on the plate holding section in a movable manner.

As a light source for the erasing section, there are given linear light sources such as a light emitting diode, a halogen lamp, a fluorescent lamp and a xenon lamp as a preferable example. However, the invention is not limited to the foregoing. Among these light sources, a light emitting diode, a halogen lamp, a fluorescent lamp and a xenon lamp are preferable as a light source for the erasing section, and a light emitting diode, in particular, is preferable from the viewpoint of easy control of emission, quantity of emitted light and power consumption. Preferable examples of the material of such light emitting diode include GaP, GaAsP/GaP and GaAlAs to which, however, the invention is not limited. The light emitting diode having a wavelength of emitted light ranging from 600 nm to 770 nm is preferable.

BRIEF DESCRIPTION OF THE DRAWINGS

FIG. 20 is a diagram showing a type to conduct sub-scanning by fixing plate holding section 4 and by moving image reading section 5 in the Y-direction.

FIG. 23 is a diagram showing a type to conduct sub-scanning by fixing plate holding section 4 holding a storage phosphor plate and by moving image reading section 5 in the vertical direction.

DETAILED DESCRIPTION OF THE PREFERRED EMBODIMENT

Concrete examples of the invention are shown below as an embodiment, but the invention is not limited to them. Though there are some decisive expression for terminology in the embodiment, they indicate preferable examples of the invention and they do not limit the meaning of terminology and technical scope of the invention.

Embodiment 1

Figure 1:
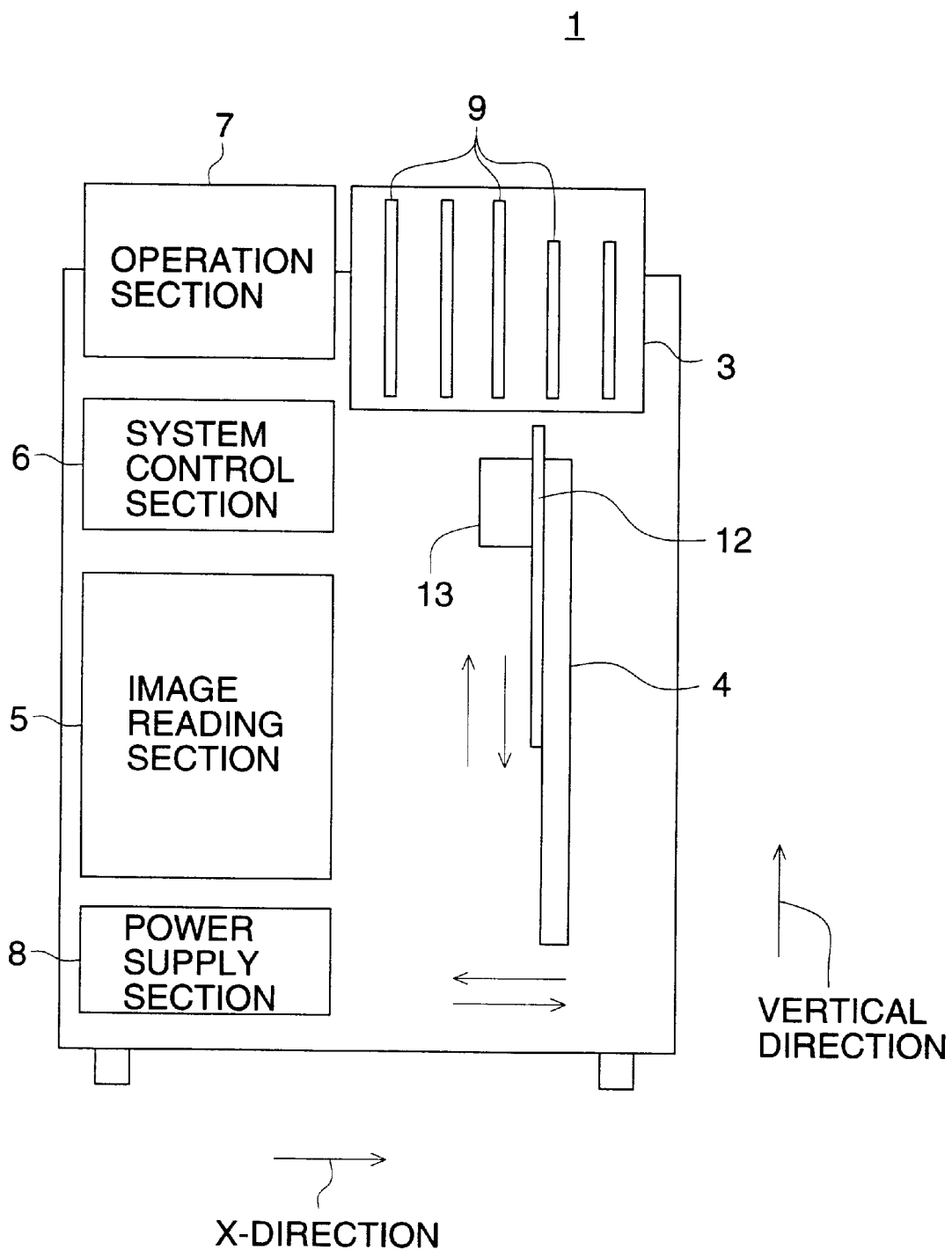
FIG. 1 is a schematic structure diagram of a radiographic image reading apparatus in the embodiment.
Figure 2:
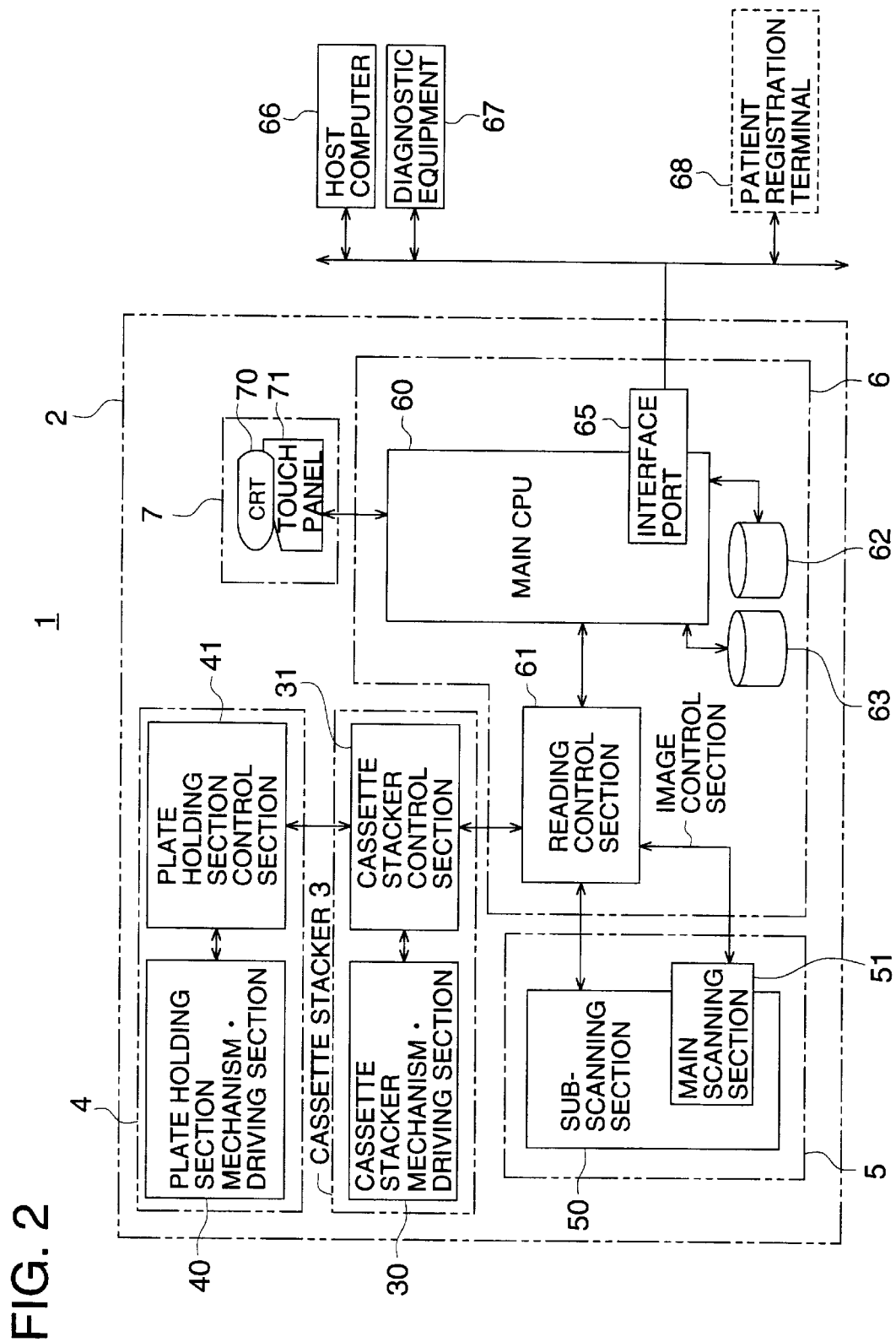
FIG. 2 is a control block diagram of a radiographic image reading apparatus in the embodiment.

A radiographic image reading apparatus in the present embodiment will be explained as follows, referring to FIG. 1 representing a schematic structure diagram of the radiographic image reading apparatus in the embodiment, FIG. 2 representing a control block diagram and FIG. 11 and FIG. 20 each representing a schematic perspective view (wherein the perspective is used).

Incidentally, in the present embodiment, a lateral direction of apparatus main body 2 of radiographic image reading apparatus 1 is called X-direction, and a longitudinal direction of apparatus main body 2 of radiographic image reading apparatus 1 is called Y-direction. Therefore, the X-direction and Y-direction are two directions which intersect each other at right angles on a horizontal plane, and an angle between the X-direction and the Y-direction is a right angle.

The radiographic image reading apparatus 1 in the present embodiment is one which takes out storage phosphor plate 12 from portable cassette 9 containing flat and storage phosphor plate 12 as a medium subjected to radiographing, and reads radiographic images recorded on the storage phosphor plate 12. On the apparatus main body 2 of radiographic image reading apparatus 1 in the present embodiment, there are provided cassette stacker 3, plate holding section 4, image reading section 5, system control section 6 as a holding section, operation section 7 and power supply section 8.

On the cassette stacker 3, a plurality of cassettes 9 each containing flat and storage phosphor plate 12 subjected to radiographing can be set side by side, in the manner that the image surface of the storage phosphor plate 12 contained is perpendicular to the X-direction, namely the image surface of the storage phosphor plate 12 is in parallel with a plane formed by the vertical direction and the Y-direction, and each storage phosphor plate 12 is different from others in terms of position in the X-direction.

The cassette stacker 3 has therein cassette stacker mechanism driving section 30 and cassette stacker control section 31, and the cassette stacker control section 31 controls so that the cassette stacker mechanism driving section 30 can take out the storage phosphor plate 12 from cassette 9 set in the cassette stacker 3 and can load the storage phosphor plate 12 into cassette 9 set in the cassette stacker 3 based on control signals coming from system control section 6.

The plate holding section 4 can take out storage phosphor plate 12 in the vertical direction from any cassette 9 set in the cassette stacker 3, and can hold it.

The plate holding section 4 has therein plate holding section mechanism driving section 40 and plate holding section control section 41, and the plate holding section control section 41 controls so that the plate holding section mechanism driving section 40 can take out the storage phosphor plate 12 from cassette 9 set in the cassette stacker 3 and can load the storage phosphor plate 12 into cassette 9 set in the cassette stacker 3 and can move based on control signals coming from system control section 6.

Image reading section 5 has therein sub-scanning section 50 and main scanning section 51. The main scanning section 51 is one which conducts main scanning MS by a laser beam in the vertical direction and reads radiographic images recorded on storage phosphor plate 12 through laser scanning. The sub-scanning section 50 is one which makes the main scanning section 51 to move in the Y-direction for sub-scanning.

The system control section 6 is equipped with main CPU 60, reading control section 61, disk for system 62, disk for image 63 and board for interface (hereinafter referred to as I/F board) 65. To the main CPU 60, there are connected CRT 70 and touch panel 71 both on operation section 7, reading control section 61 of system control section 6, disk for system 62, disk for image 63 and I/F board 65.

In the disk for system 62, there is stored s system program with which the main CPU 60 conducts overall control, image processing, image transmission control and image control. In the disk for image 63, there are stored images sent from the reading control section 61 and images subjected to image processing.

The main CPU 60 causes images sent from the reading control section 61 and images subjected to image processing to be stored in the disk for image 63 while developing system program stored in the disk for system 62 on an internal memory, and conducts overall control, image processing, image transmission and image control while reading images stored in the disk for image 63.

The reading control section 61 controls cassette stacker control section 31, plate holding section control section 41, sub-scanning section 50 and main scanning section 51, then causes radiographic images recorded on storage phosphor plate 12 to be read through laser scanning, then receives image signals from the main scanning section 51, and sends images thus read to the main CPU 50.

The main CPU 60 is connected, through I/F board 65, to host computer 66, diagnostic equipment 67 and patient registration terminal 68 which are located outside apparatus main body 2. Thereby, the main CPU 60 transmits images to host computer 66, diagnostic equipment 67 and patient registration terminal 68 through I/F board 65.

The operation section 7 has therein CRT 70 and touch panel 71, and the CRT 70 displays display images transmitted from the main CPU, while the touch panel 71 sends information related to direction input inputted through touching by an operator to the main CPU 60.

The main CPU 60 conducts overall control, image processing, image transmission and image control, based on information related to direction input sent from the touch panel 71 of the operation section 7, and transmits display images properly to CRT 70 for displaying necessary information on CRT 70.

Then, when direction input including direction contents for designating either cassette 9 set in the cassette stacker 3 is conducted from operation section 7, system control section 6 controls plate holding section 4 holding storage phosphor plate 12 and image reading section 5 so that the plate holding section 4 may take out storage phosphor plate 12 in the vertical direction from cassette 9 designated by direction input from operation section 7 and may hold it, while the image reading section 5 may read radiographic images recorded on the storage phosphor plate 12 through laser scanning.

Namely, as shown in FIG. 20, the image reading section 5 moves in the X-direction, in the first place (S1), to the prescribed position in the X-direction where the plate holding section 4 can take out storage phosphor plate 12 in the vertical direction from cassette 9 designated by direction input from operation section 7, then, takes out the storage phosphor plate 12 in the vertical direction from cassette 9 designated by direction input from operation section 7 at the prescribed position in the X-direction, and holds the storage phosphor plate 12 (S2), and in the third place (S3), the plate holding section 4 is made to move at least in the X-direction and to stop at the prescribed position in the X-direction, then in the fourth place (s4), the plate holding section 4 holding the storage phosphor plate 12 is fixed, and the image reading section 5 is moved in the Y-direction, thereby, the storage phosphor plate 12 is subjected to sub-scanning, and the image reading section 5 reads radiographic images recorded on the storage phosphor plate 12 held by the plate holding section 4.

Due to this, in cassette stacker 3, storage phosphor plate 12 is almost perpendicular to the X-direction, and plural cassettes 9 can be set side by side so that their positions in the X-direction may be different each other. Therefore, while taking the storage phosphor plate 12 out of one cassette 9, another cassette can be set at another setting position, which leads to improved work efficiency.

In addition to this, plate holding section 4 can take out storage phosphor plate in the vertical direction from any cassette 9 set in the cassette stacker 3, and can hold it. Therefore, even when arranging so that storage phosphor plate 12 having a larger area may also be read, a larger floor space is not required, and no space is required in the periphery of the position of installation in the horizontal direction, and it hardly happens that the cassette 9 which is wrongly set is hit or something is thrown at it.

Further, since the plate holding section 4 holding storage phosphor plate 12 and the image reading section 5 have only to be moved in the X-direction and set at the prescribed relative position in the X-direction, it is technically easy to set at the prescribed relative position which is required by laser scanning.

Further, since the image reading section 5 is fixed, it is easy to arrange so that accurate image reading can be performed stably for a long time. When reading images, the image reading section 5 is fixed, and the plate holding section 4 is moved relatively in the Y-direction for sub-scanning. Therefore, the sub-scanning does not require the movement accompanied by gravity load, and stable sub-scanning can be conducted, which easily makes read images to be excellent ones.

It is further unnecessary to bend storage phosphor plate 12 to transport it, and only one image reading section 5 is enough.

In the fifth place (S5), when the image reading section 5 finishes reading radiographic images recorded on the storage phosphor plate 12 that is held by the plate holding section 4, the plate holding section 4 moves in the X-direction to the prescribed position in the X-direction where the storage phosphor plate 12 held by the plate holding section 4 can be conveyed to and loaded in the cassette 9 which had contained the storage phosphor plate 12 and is set in cassette stacker 3 in the vertical direction, and conveys, in the vertical direction, the storage phosphor plate 12 held from which the radiographic images thereon have been read by the image reading section 5 to the cassette 9 which had contained the storage phosphor plate 12 to contain the storage phosphor plate 12 in the cassette 9 (S6).

Due to this, only one plate holding section 4 can load in any cassette 9 set in cassette stacker 3 the storage phosphor plate 12 which has been taken out, which makes the structure simple.

On the top end portion of the plate holding section 4, there is provided erasing section 13. When the plate holding section 4 conveys, in the vertical direction, the storage phosphor plate 12 held from which the radiographic images thereon have been read by the image reading section 5 to the cassette 9 in which the storage phosphor plate 12 had been loaded, to load the storage phosphor plate 12 in the cassette 9, the erasing section 13 erases residual images remaining on the storage phosphor plate 12 from which the radiographic images thereon have been read by the image reading section 5, by irradiating erasing light on the storage phosphor plate 12.

Due to this, both loading the storage phosphor plate 12 in cassette 9 and erasing residual images remaining on the storage phosphor plate 12 can be conducted simultaneously, which can shorten the cycle time for image reading.

Next, cassette 9 used in radiographic image reading apparatus 1 will be explained in detail.

Figure 3:
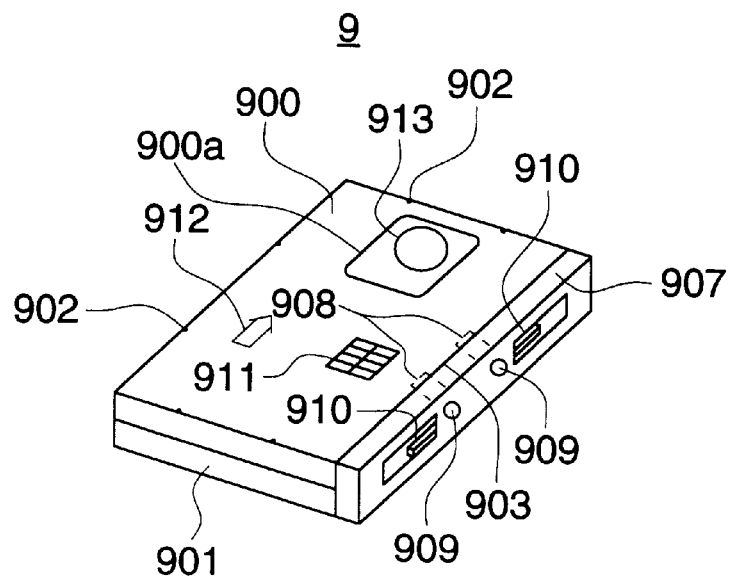
FIG. 3 is a perspective view showing how storage phosphor plate 12 is loaded in cassette 9 in the embodiment.
Figure 4:
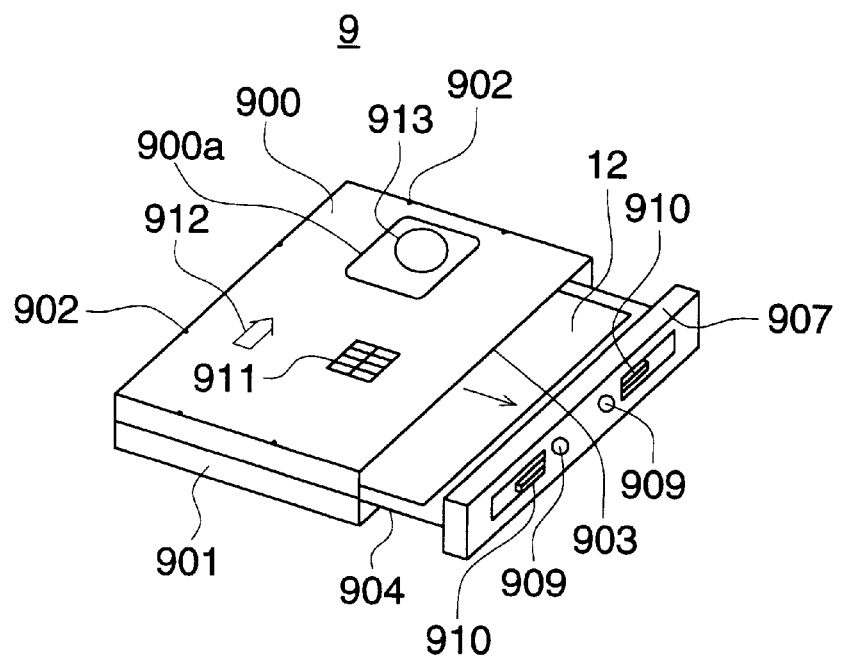
FIG. 4 is a perspective view showing the state wherein storage phosphor plate 12 is drawn out cassette 9 in the embodiment.
Figure 5:
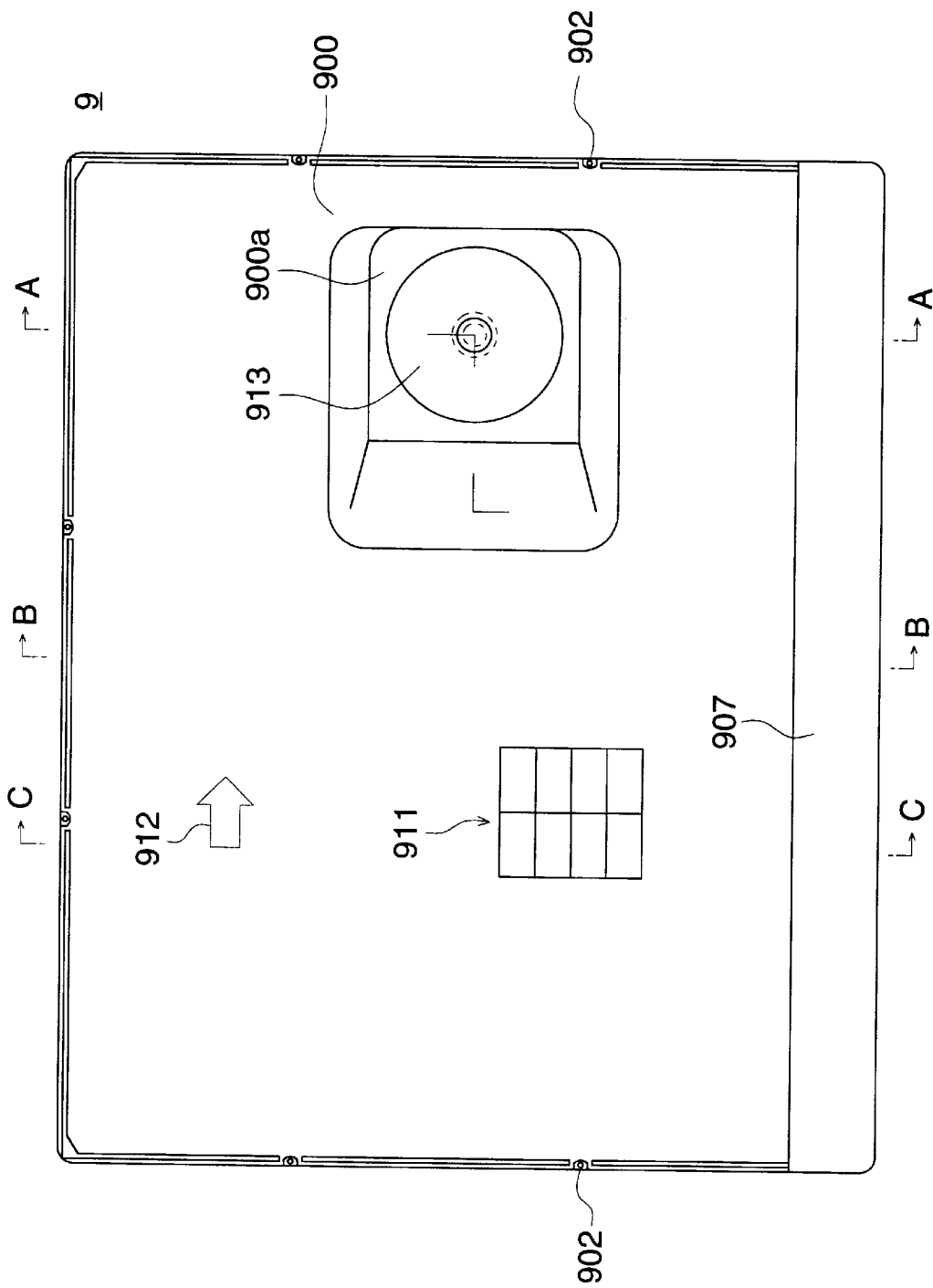
FIG. 5 is a plan view of cassette 9 in the embodiment.
Figure 6:
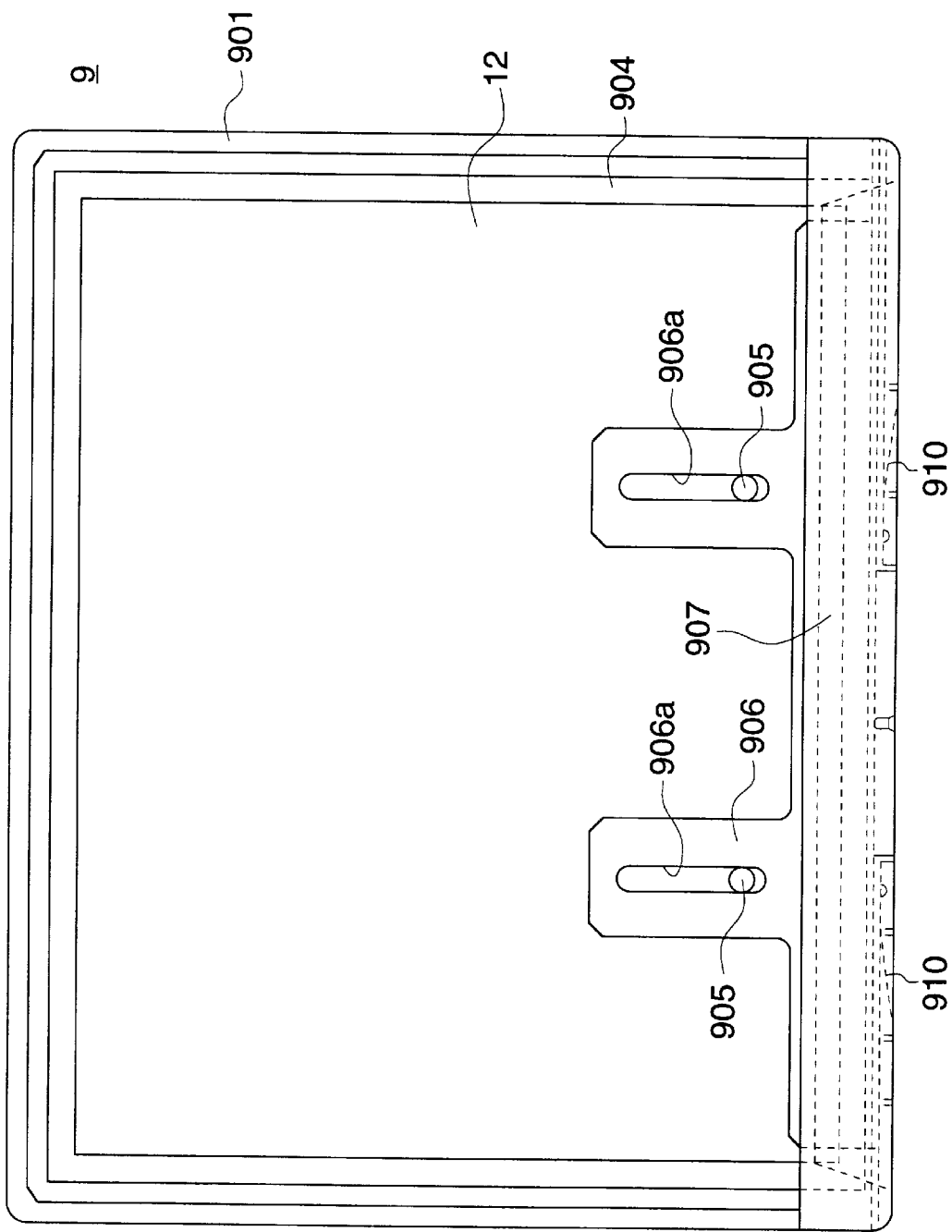
FIG. 6 is a plan view showing how storage phosphor plate 12 is loaded in cassette 9 in the embodiment.
Figure 7:
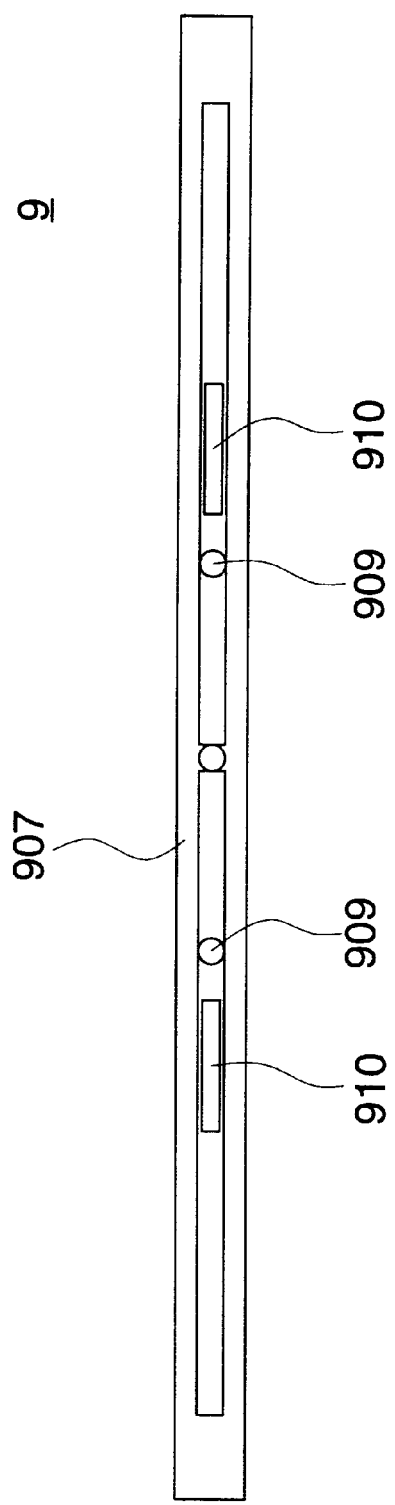
FIG. 7 is a side view of cassette 9 in the embodiment.
Figure 8:
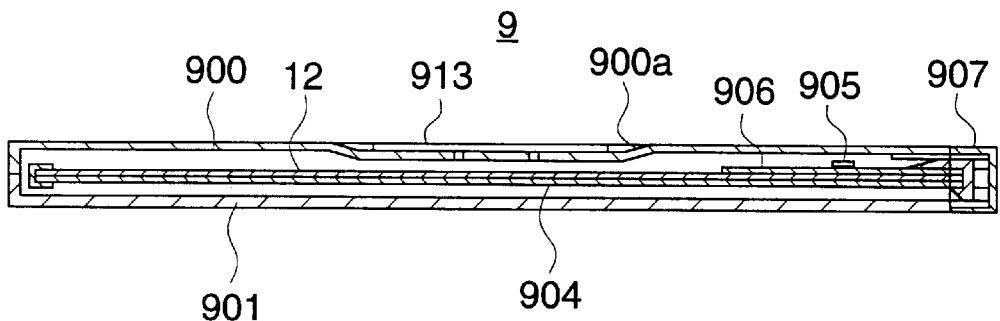
FIG. 8 is a sectional view taken on line A—A in FIG. 5.
Figure 9:
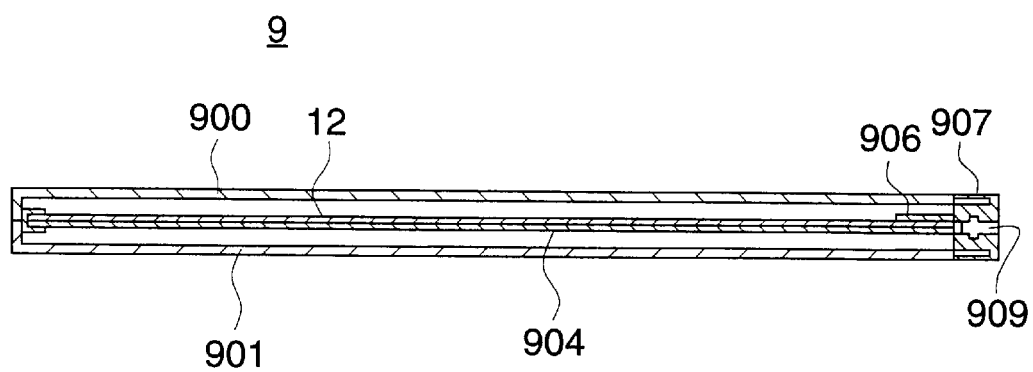
FIG. 9 is a sectional view taken on line B—B in FIG. 5.
Figure 10:
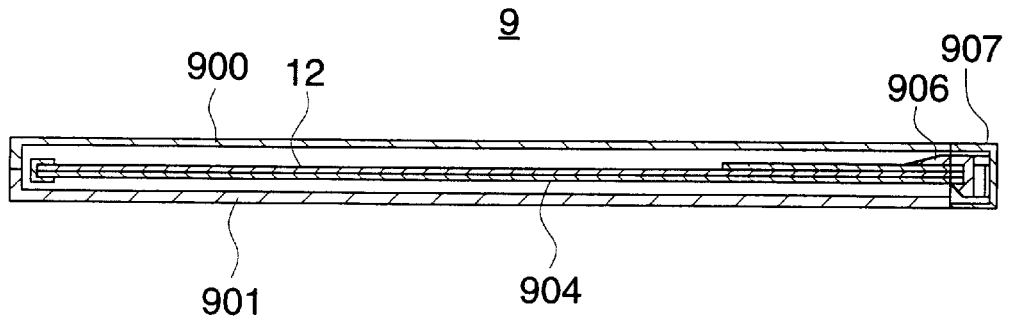
FIG. 10 is a sectional view taken on line C—C in FIG. 5.

Cassette 9 containing therein storage phosphor plate 2 is structured as shown in FIG. 3–FIG. 10, wherein FIG. 3 is a perspective view showing how storage phosphor plate 12 is loaded in cassette 9, FIG. 4 is a perspective view showing the state wherein storage phosphor plate 12 is drawn out cassette 9, FIG. 5 is a plan view of cassette 9, FIG. 6 is a plan view showing how storage phosphor plate 12 is loaded in cassette 9, FIG. 7 is a side view of cassette 9, FIG. 8 is a sectional view taken on line A—A in FIG. 5, FIG. 9 is a sectional view taken on line B—B in FIG. 5 and FIG. 10 is a sectional view taken on line C—C in FIG. 5.

Cassette 9 is composed of case halves 900 and 901 which are united solidly with their peripheral portions clamped with machine screws 902. On one side portion of the cassette 9, there is formed opening 903 through which storage phosphor plate 12 can be drawn out.

The storage phosphor plate 12 has a stimulating phosphor layer. A stimulating phosphor is one of storage phosphors which accumulate energy in accordance with radiation transmissivity distribution of a subject for a quantity of radiation irradiated from a radiation generating source, and thereby form a latent image. On the storage phosphor plate 12, a stimulating phosphor layer is provided through gas phase sedimentation or coating. The stimulating phosphor layer is shielded or covered by a protecting member so that the stimulating phosphor layer may be shielded from an adverse effect caused by environmental conditions or from damage. Examples of stimulating phosphors used include;

$$M'X \cdot aM''X_2 \cdot bM'''X_5 : cA$$

(wherein, M' is at least one kind of an alkali metal selected from Li, Na, K, Rb and Cs, M" is at least one kind of a divalent metal selected from Be, Mg, Ca, Sr, Ba, Zn, Cd, Cu and Ni, M''' is at least one kind of halogen selected from Sc, Y, La, Ce, Pr, Nd, Pm, Sm, Eu, Gd, Tb, Dy, Ho, Er, Tm, Yb, Lu, Al, Ga and In, A is at least one kind of a metal selected from Eu, Tb, Ce, Tm, Dy, Pr, Ho, Nd, Yb, Er, Gd, Sc, Lu, Sm, Y, Tl, Na, Ag, Cu and Mg, and "a" represents values within a range of $0<a<0.5$, "b" represents values within a range of $0 \leq a<0.5$ and "c" represents values within a range of $0<a<0.2$), alkaline earth metal fluorohalide phosphor expressed with $(Ba_{1-x-y} Mg_x Ca_y) FX:eEu^2$ (wherein, X is one of Br and Cl, x, Y and e represent values satisfying respectively conditions of $0<x+y<0.6$, $xy \approx 0$ and $10^{-6} \leq e \leq 5 \times 10^{-2}$), and $$BAFX:xCe, yA$$

(wherein, X is at least one of ClBr and I, A is at least one of ln, Tl, Gd, Sm and Zn, and x and y represent respectively $0<x \leq 2 \times 10^{-1}$ and $0<y<5 \times 10^{-2}$.)

The storage phosphor plate 12 fixed on a rigid tray 904 located inside cassette 9, a pair of engagement pins 905 are provided on the tray 904 corresponding to the portion other than an area where images are recorded, and these paired engagement pins 905 are penetrating through the storage phosphor plate 12. For the paired engagement pins 905, there are provided guide holes 906a of guide plate 906, and cap 907 which covers openings is provided on the guide plate 906.

Locking mechanism 908 is built in the cap 907, and locking by the locking mechanism 908 can be canceled through locking hole 909. Further, on the cap 907, there are provided a pair of levers 910, and these paired levers 910 open and close the cap 907 so that storage phosphor plate 12 is drawn out of or loaded in the cassette 9.

Types and sizes of cassette 9 are shown in Table 1.

TABLE 1

| Cassette Types | Cassette size (mm) Height × Depth | Thickness (mm) | Weight (g) |
| --- | --- | --- | --- |
| 14 × 17 in. (345 × 430 mm size) | 383.5 × 459.5 | 14 | 2400 |
| 14 × 14 in. (345 × 345 mm size) | 383.5 × 383.5 | | 1900 |
| 10 × 12 in. (254 × 305 mm size) | 281.5 × 332.5 | | 1200 |
| 8 × 10 in. (200 × 251 mm size) | 230.5 × 281.5 | | 900 |
| 24 × 30 | 267.5 × 327.5 | | 1200 |
| 18 × 24 in. for mammography use | 194.5 × 267.5 | | 800 |

On cassette 9, there is pasted identification seal 911 on which identification information of black and white is recorded. Through detection of the identification information on the identification seal 911, types and sizes of cassette 9 are detected, and erroneous loading in cassette stacker 3 is detected.

Though indication of upper and lower grid direction of cassette 9 depends on indication mark 912 for the upper or lower direction, it is also possible to arrange so that the upper or lower direction can be designated by loading the cassette 9 in the cassette stacker 3 with cap 907 facing downward.

On the cassette 9, there is provided diagnosis record clip 913 on case half 900, and around the diagnosis record clip 913, there is formed recessed portion 900a on the case half 900, and diagnosis records are held between the recessed portion 900a and the diagnosis record clip 913.

Next, a cassette stacker, plate holding section 4, image reading section 5, system control section 6, operation section 7 and power supply section 8 which are provided on apparatus main body 2 of radiographic image reading apparatus 1 will be explained in detail.

Figure 11:
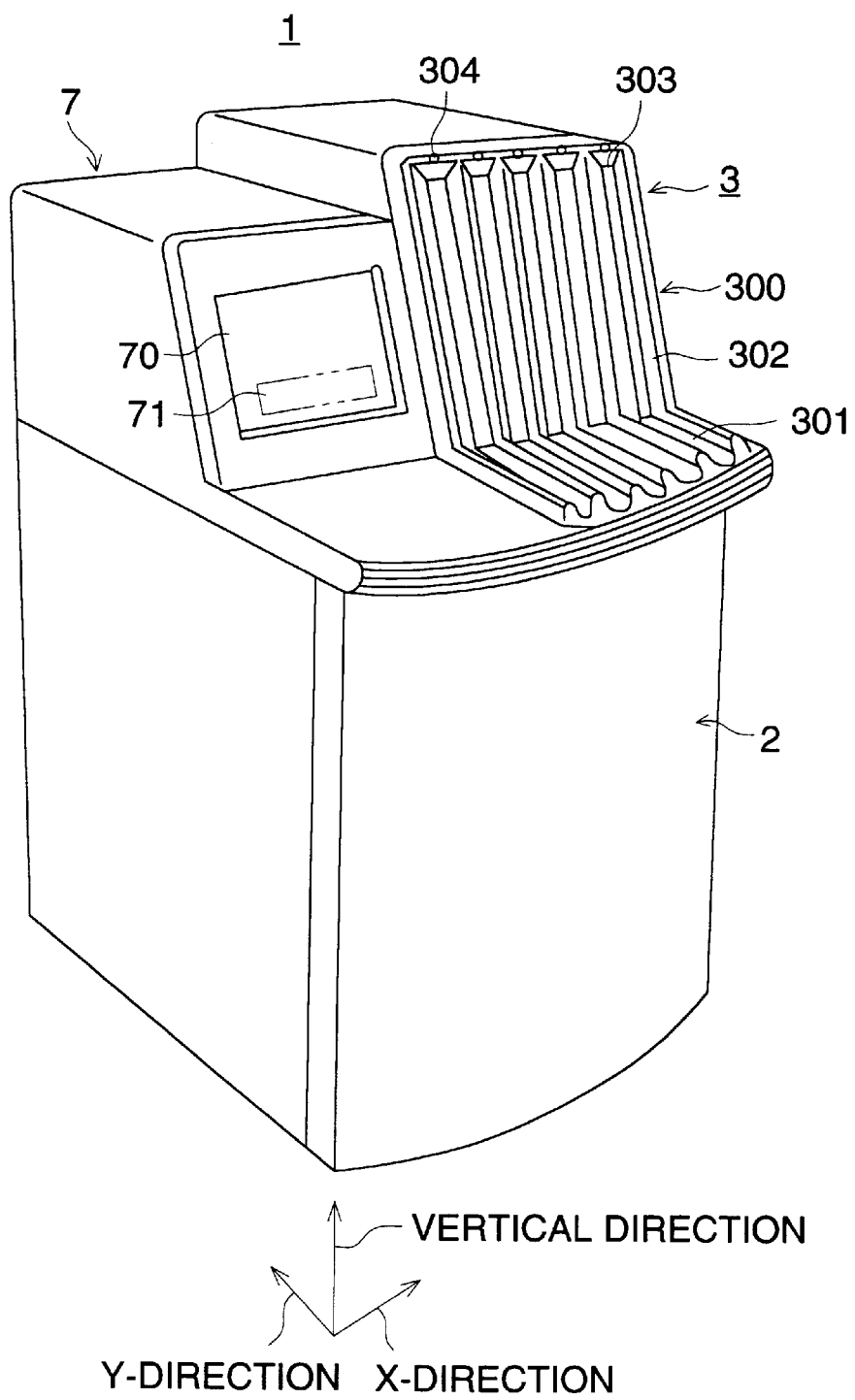
FIG. 11 is a perspective view of a radiographic image reading apparatus in the embodiment.
Figure 12:
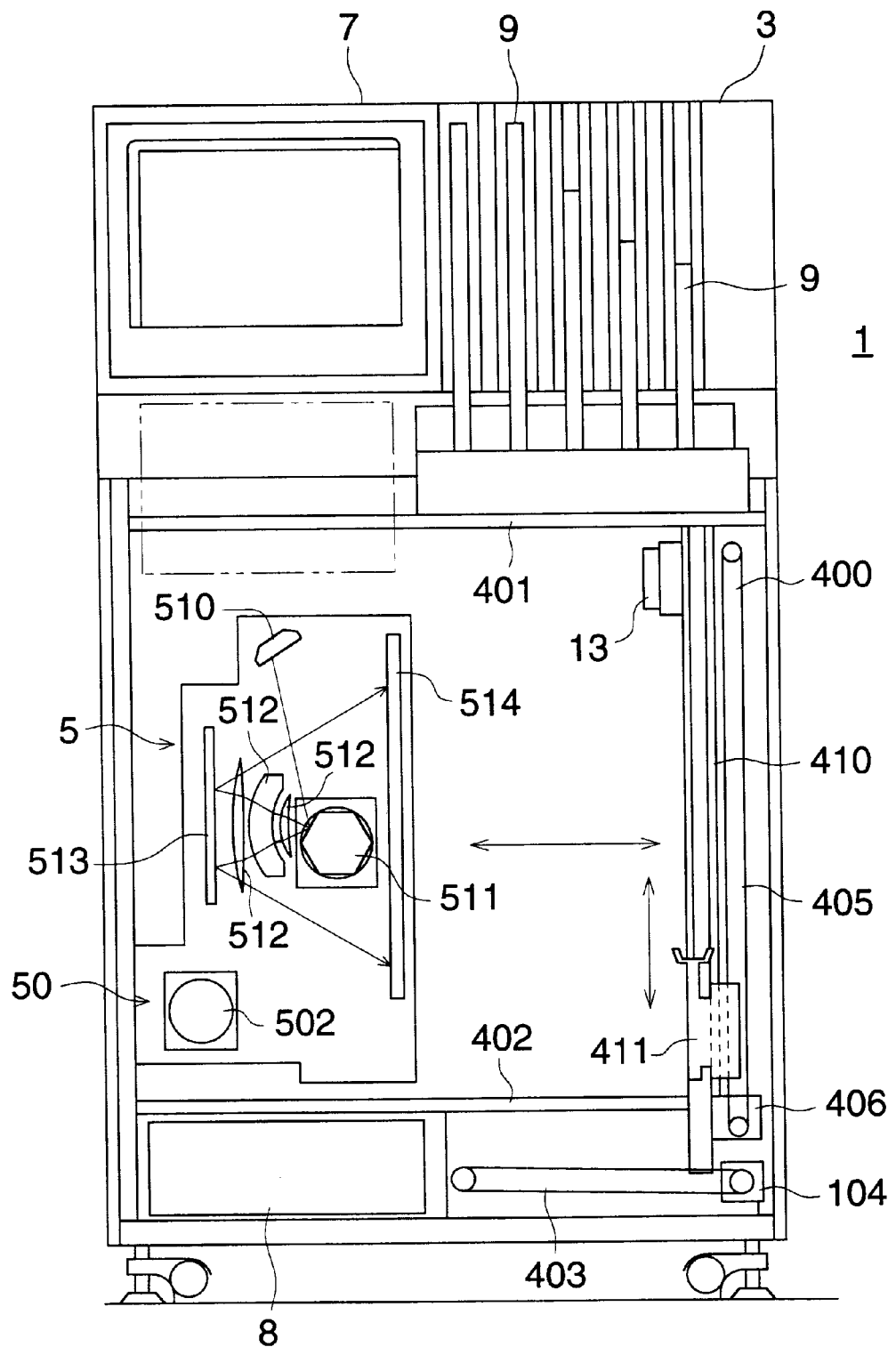
FIG. 12 is a front view of a radiographic image reading apparatus in the embodiment.
Figure 13:
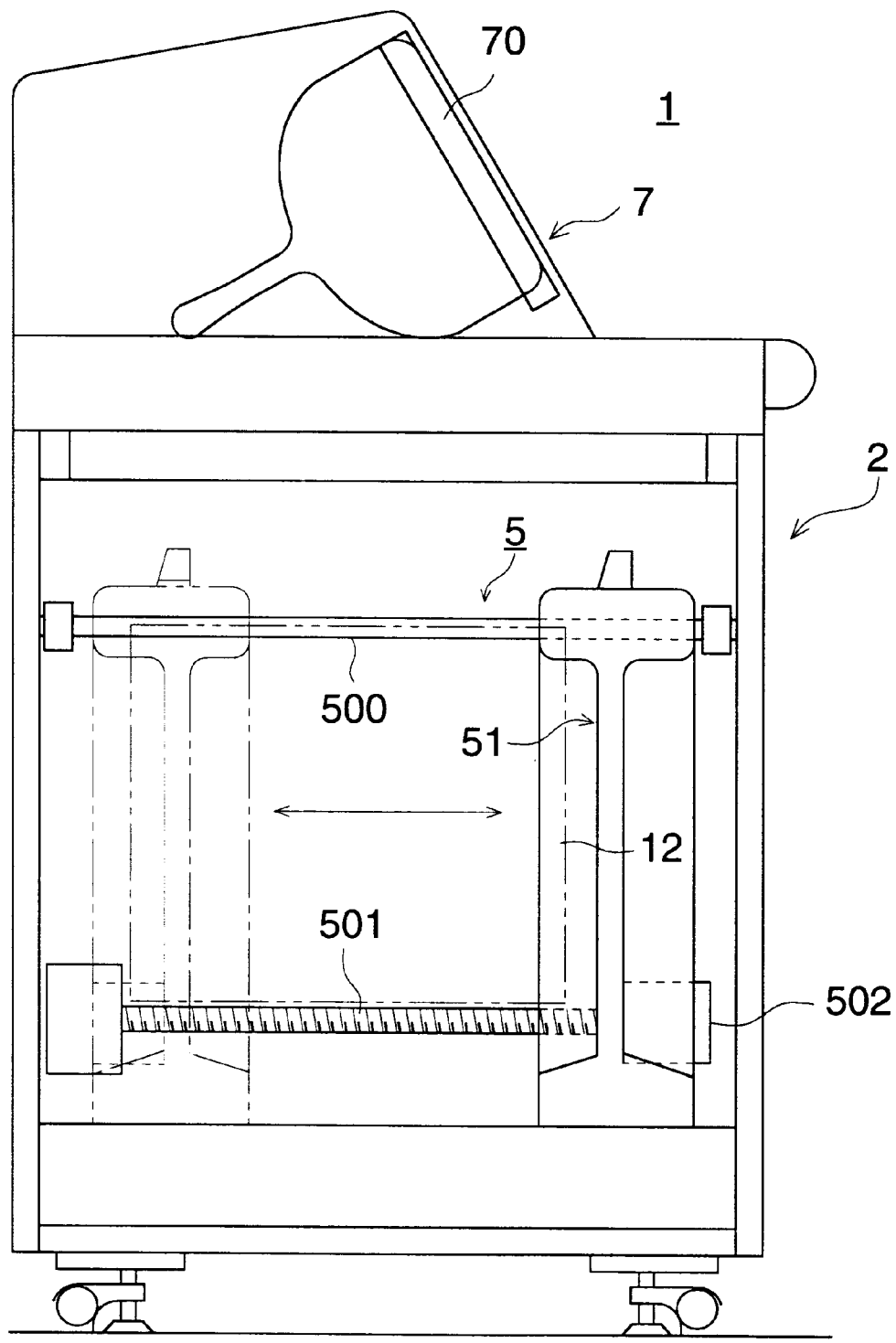
FIG. 13 is a left side view of a radiographic image reading apparatus in the embodiment.
Figure 14:
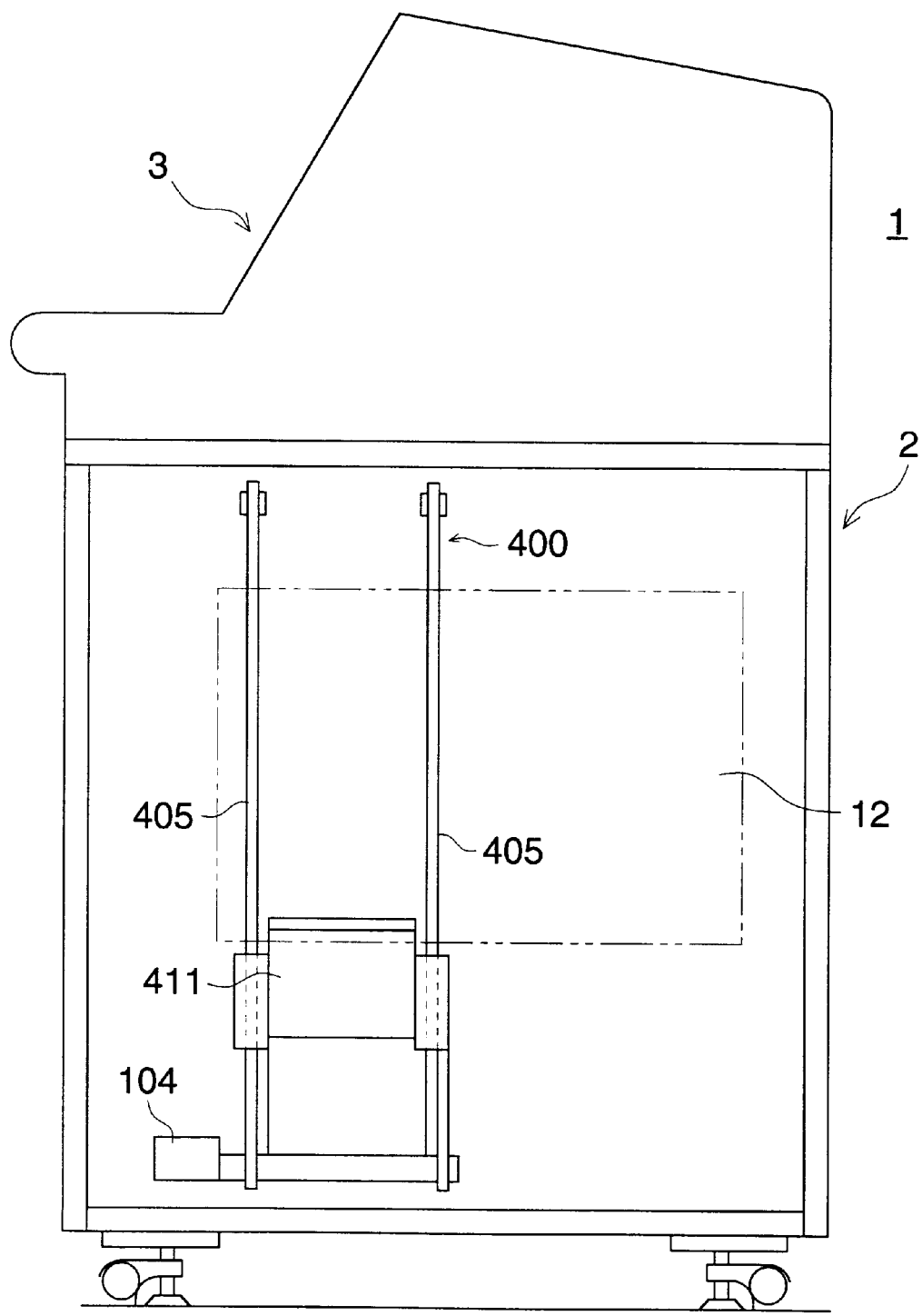
FIG. 14 is a right side view of a radiographic image reading apparatus in the embodiment.
Figure 15:
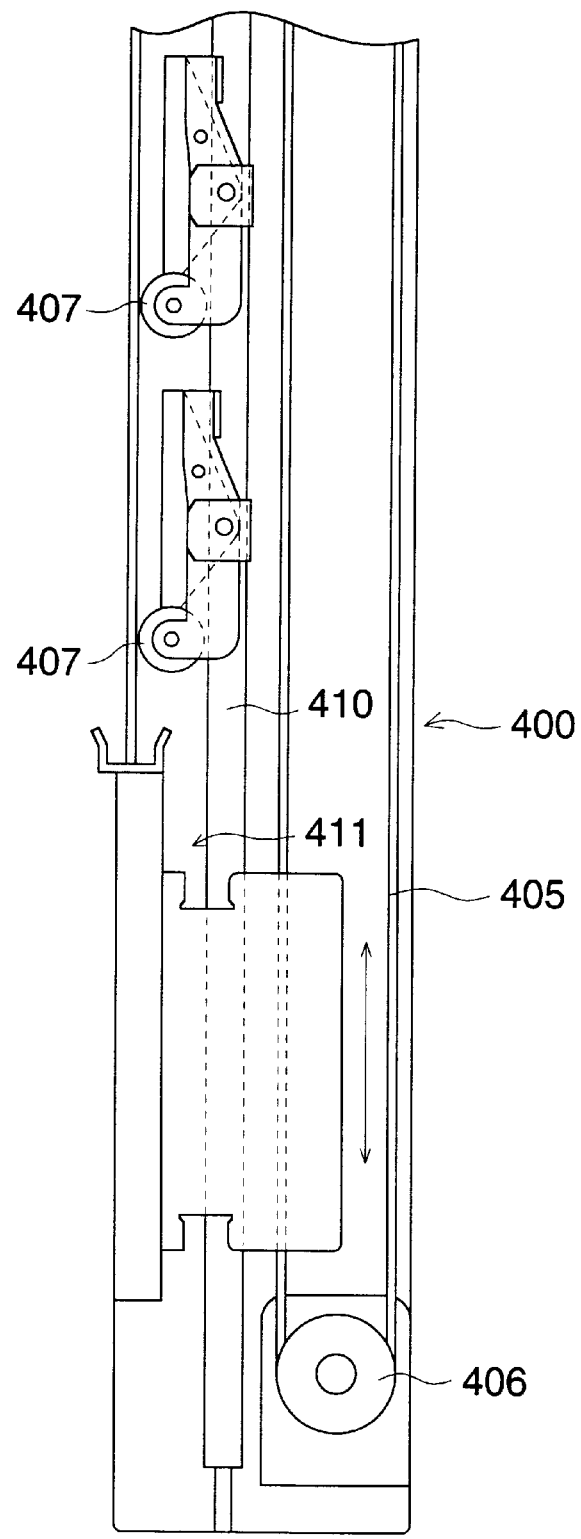
FIG. 15 is a front view of a plate holding section of a radiographic image reading apparatus in the embodiment.
Figure 16:
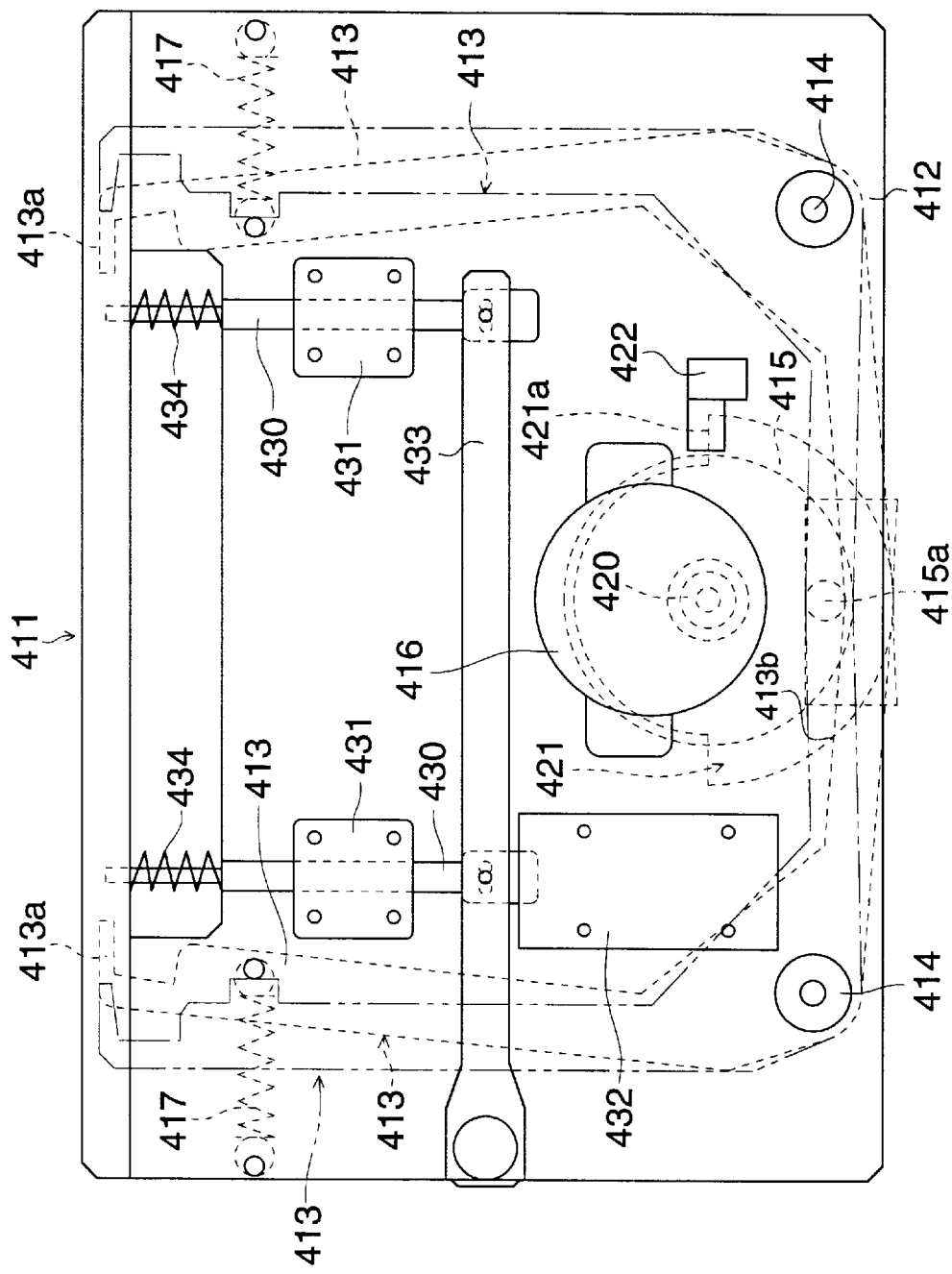
FIG. 16 is a side view of a cassette clinch of a radiographic image reading apparatus in the embodiment.
Figure 17:
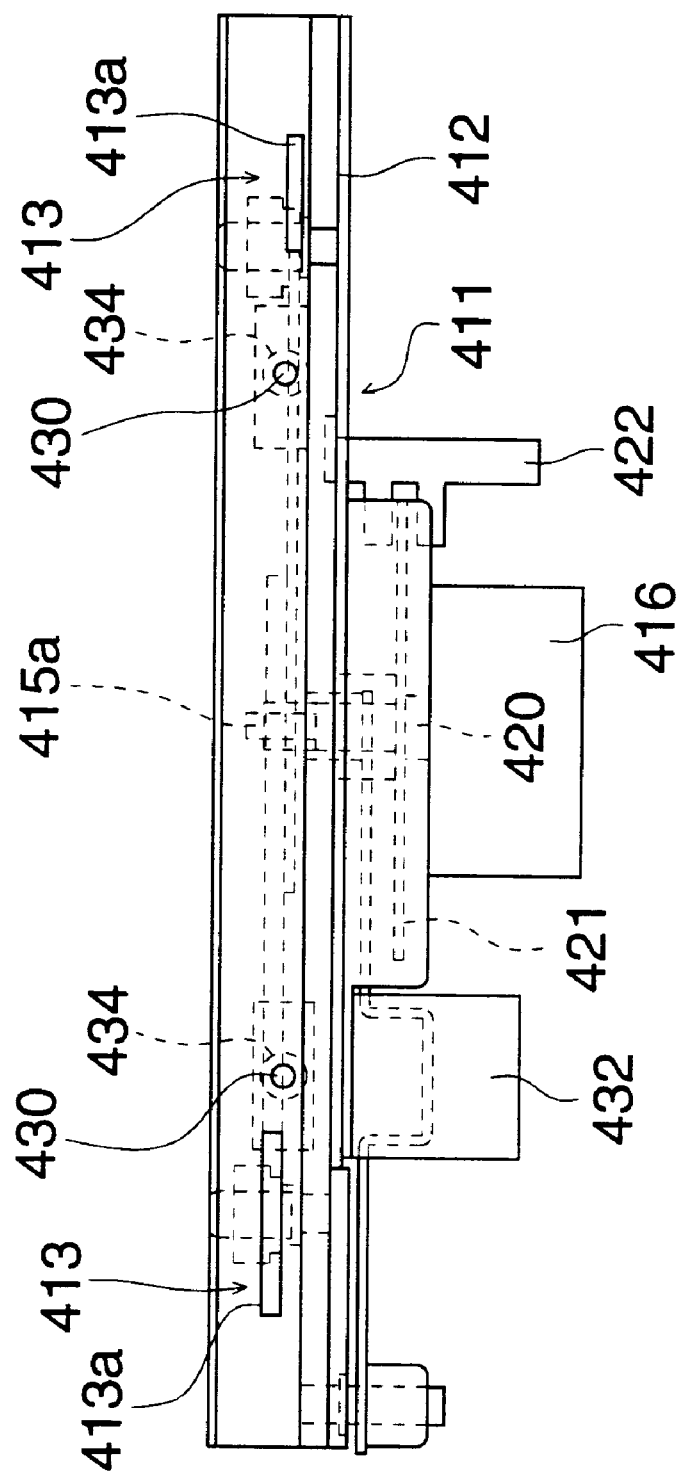
FIG. 17 is a plan view of a cassette clinch of a radiographic image reading apparatus in the embodiment.
Figure 18:
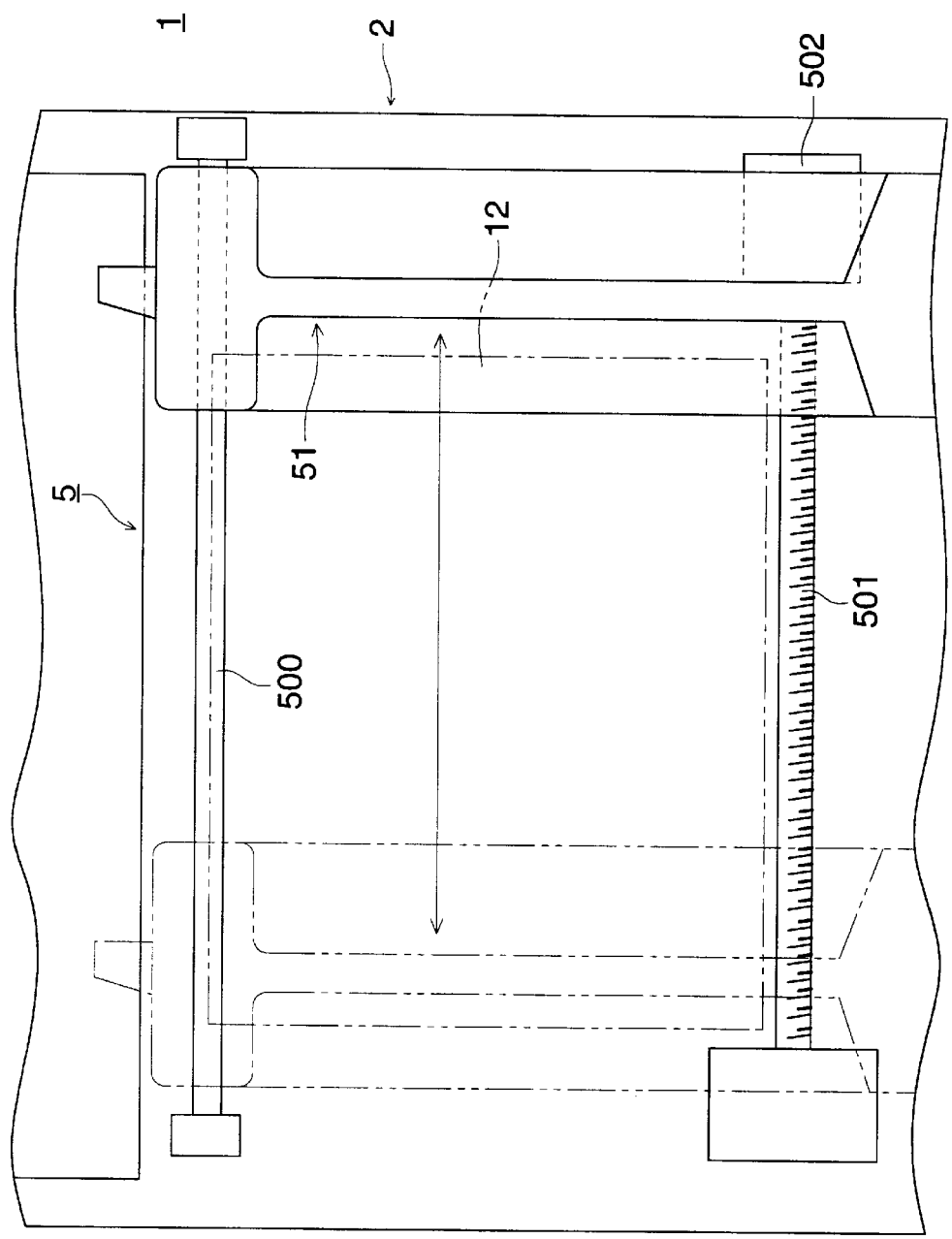
FIG. 18 is a side view of a sub-scanning section of a radiographic image reading apparatus in the embodiment.
Figure 19:
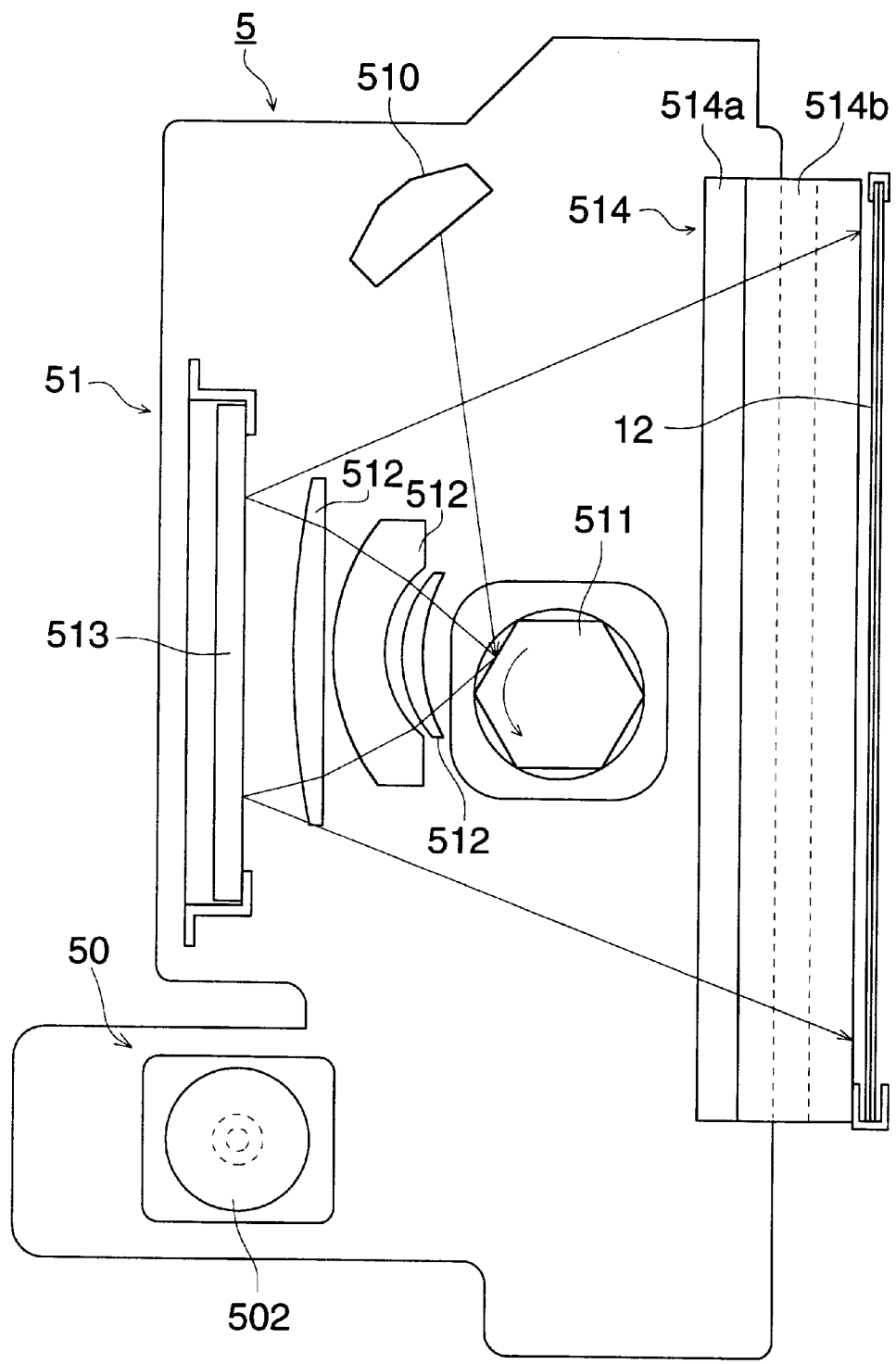
FIG. 19 is a front view showing an optical system of a main scanning section of a radiographic image reading apparatus in the embodiment.
Figure 21:
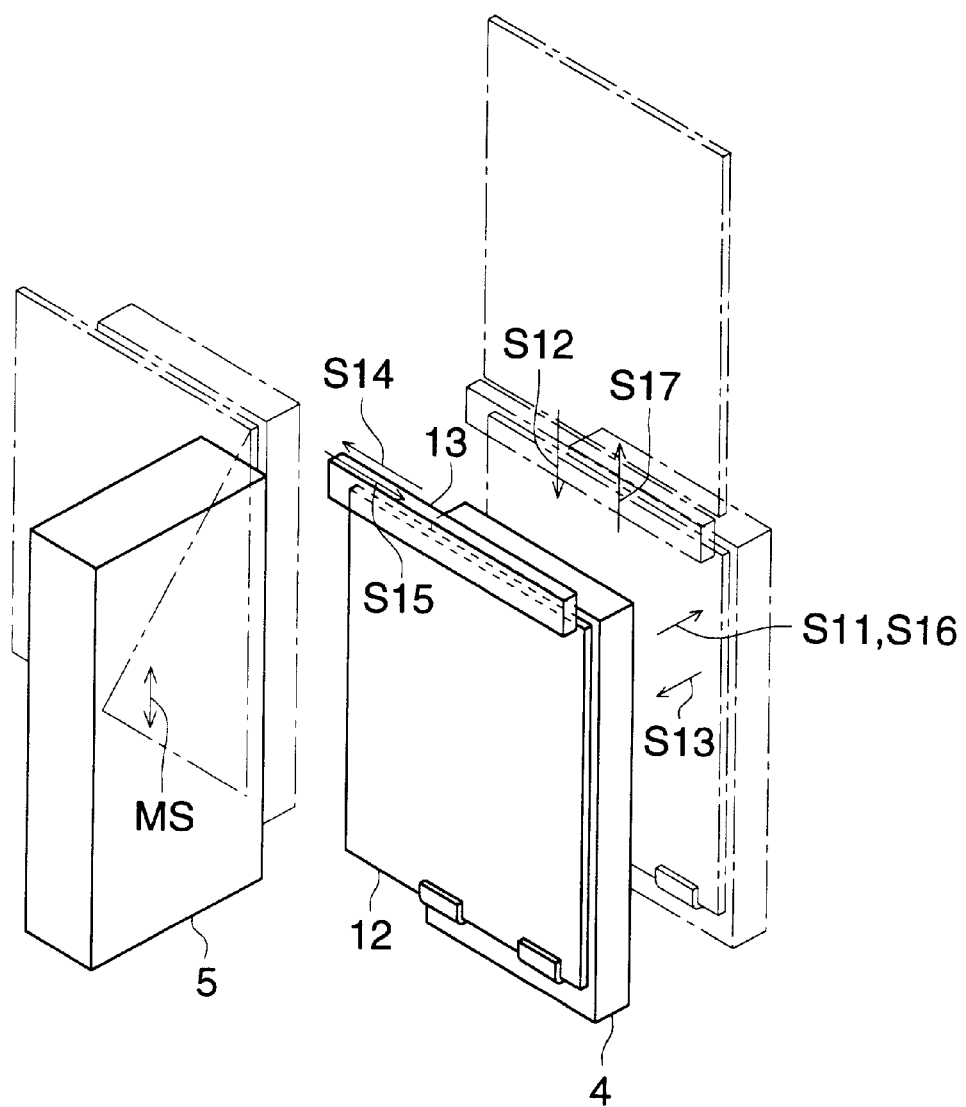
FIG. 21 is a diagram showing a type to conduct sub-scanning by fixing image reading section 5 and by moving plate holding section 4 holding storage phosphor plate 12 in the Y-direction.
Figure 22:
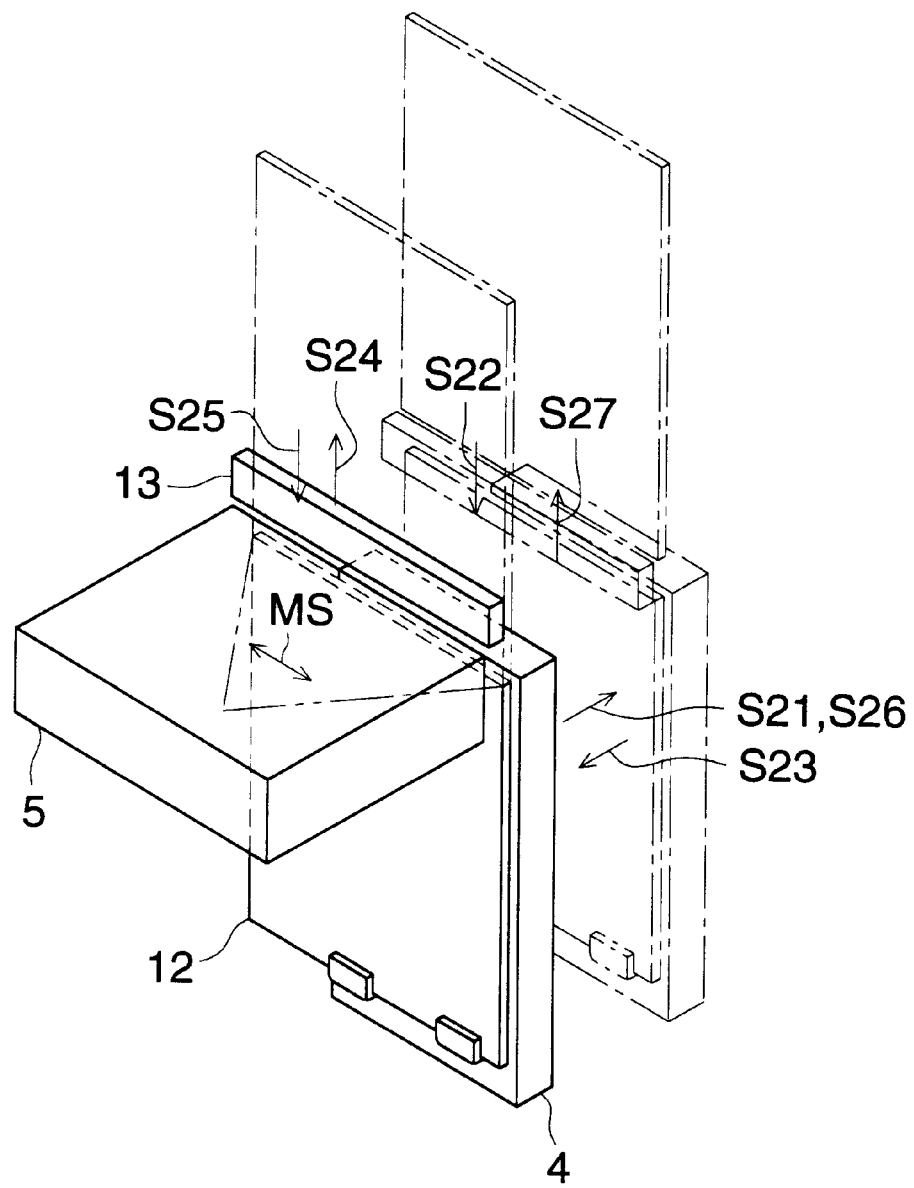
FIG. 22 is a diagram showing a type to conduct sub-scanning by fixing image reading section 5 and by moving storage phosphor plate 12 held by plate holding section 4 in the vertical direction.
Figure 24:
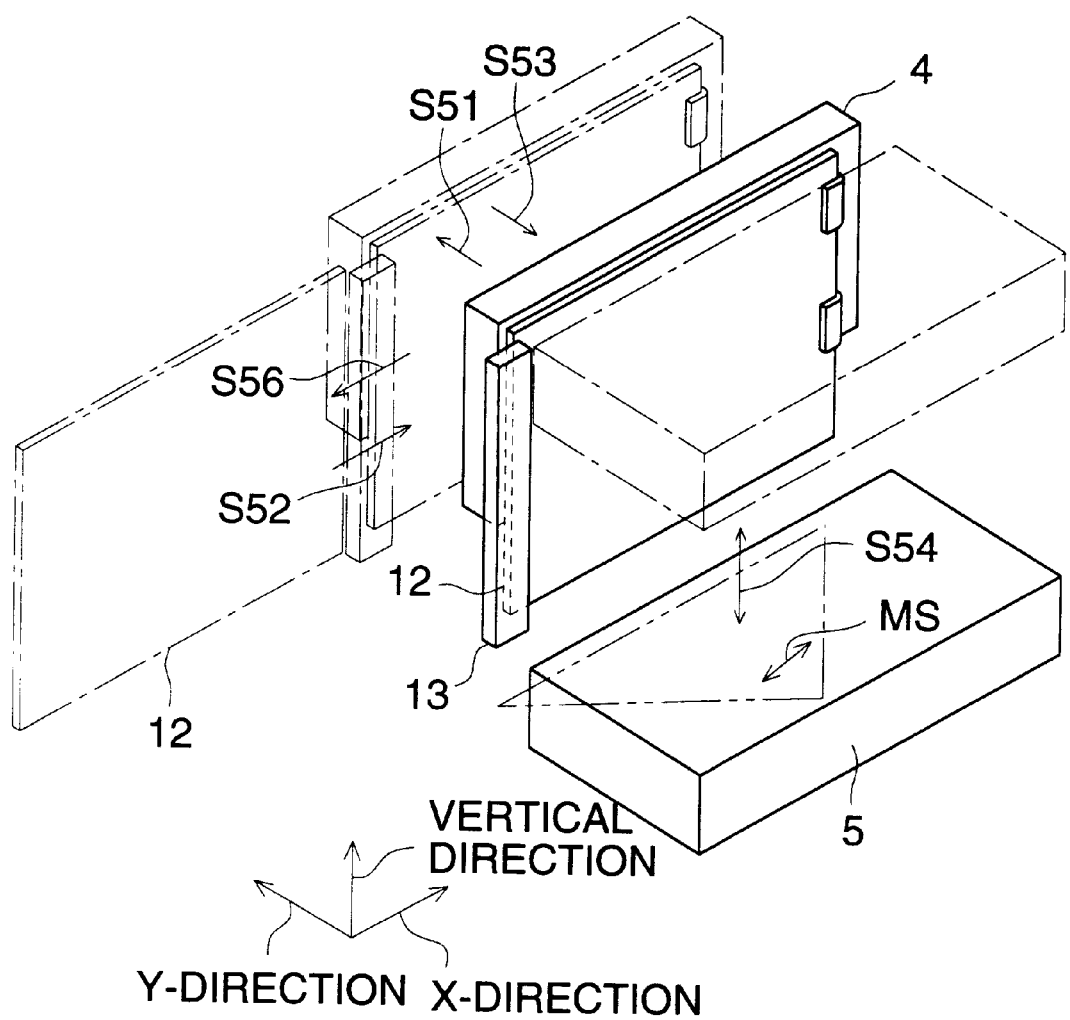
FIG. 24 is a diagram showing another type of the invention.
Figure 25:
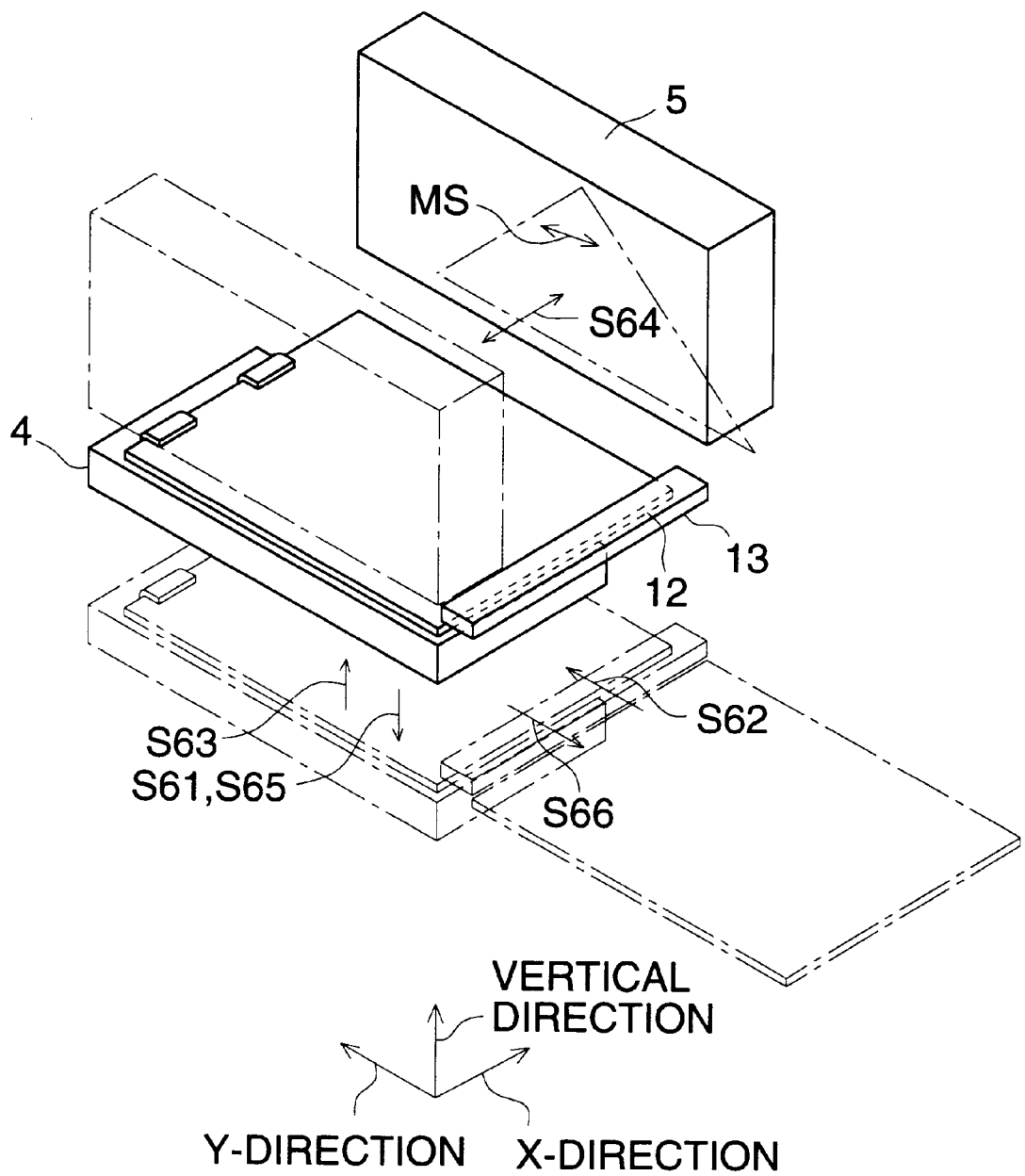
FIG. 25 is a diagram showing still another type of the invention.

FIG. 11 is a perspective view of a radiographic image reading apparatus, FIG. 12 is a front view of a radiographic image reading apparatus, FIG. 13 is a left side view of a radiographic image reading apparatus, FIG. 14 is a right side view of a radiographic image reading apparatus, FIG. 15 is a front view of a plate holding section, FIG. 16 is a side view of a cassette clinch, FIG. 17 is a plan view of a cassette clinch, FIG. 18 is a side view of a sub-scanning section, and FIG. 19 is a front view showing an optical system of a main scanning section.

First of all, cassette stacker 3 is arranged at the right hand side on the upper portion of radiographic image reading apparatus 1 and has setting section 300 which is provided for every five slots. At the left hand side on the upper portion of the radiographic image reading apparatus 1, there is arranged operation section 7, and cassette 9 can be set by loading it in cassette stacker 3 while conducting operations through the operation section 7, which makes operations to be easy.

The setting section 300 is composed of guide section 301 and loading section 302. The guide section 301 is of a groove type and it extends to the loading section 302 to be formed so that it guides cassette 9 to the loading section 302. The loading sections 302 contain and hold cassettes 9 at prescribed intervals.

Light-lock shutter 303 shields the inside except when an operator sets cassette 9 and takes out cassette 9.

The cassette stacker 3 is one wherein an operator sets cassette 9 by inserting it from this side while holding the cassette 9 vertically with its longer side being horizontal, and upon completion of setting the cassette 9, light-lock shutter 303 provided at an opening of the loading section 302 for each slot closes to prevent light from leaking through the periphery of the cassette.

On the cassette 9, there is pasted identification seal 911 so that an operator can identify the direction of loading the cassette and can identify the right side and the other side of the cassette.

It is possible to take out cassette 9 from each slot except when reading is conducted, and LED lamp 304 showing "in process of reading" is provided to prevent that cassette 9 is taken out by mistake.

Plate holding section mechanism driving section 40 provided on plate holding section 4 is structured as shown in FIG. 12, FIG. 15 or FIG. 17.

Namely, the plate holding section mechanism driving section 40 is supported on guide rails 401 and 402 each being provided on its upper and lower portions with supporting frame 400. These guide rails 401 and 402 are arranged in the direction perpendicular to cassette 9 loaded in cassette stacker 3. A lower end portion of the supporting frame 400 is fixed to conveyance belt 403 which is arranged at the lower portion, and the conveyance belt 403 is driven by conveyance motor 404, whereby the supporting frame 400 moves along the guide rails 401 and 402.

On the upper portion of the supporting frame 400, there is attached erasing section 13. As an erasing light source of the erasing section 13, two 300-watt halogen lamps (driving voltage: 90 V), for example, are used, and the moving speed of storage phosphor plate 12 in the course of erasing is 10.5 mm/sec which, however, is variable depending on image recording on the storage phosphor plate 12. The halogen lamp is an erasing light source which is lit to project erasing light on the storage phosphor plate 12 to erase residual images. This erasing of residual images is projecting erasing light on the storage phosphor plate 12, and it means scanning by a laser beam and discharging of residual radiation energy on the storage phosphor plate 12 after reading.

On the supporting frame 400, there is provided guide shaft 410 vertically, and cassette clinch 411 is mounted on the guide shaft 410 to be movable vertically. The cassette clinch 411 is attached to conveyance belt 405 arranged vertically, and the conveyance belt 405 is driven by conveyance motor 406 arranged at the lower position of the supporting frame 400, thus, the cassette clinch 411 moves vertically along the guide shaft 410. Further, on the supporting frame 400, there is provided holding roller 407 which prevents the storage phosphor plate 12 from falling and holds an end portion outside an image recording area on the storage phosphor plate 12.

On the cassette clinch 411, there are provided, inside supporting member 412, a pair of arms 413 each being capable of rotating around supporting pin 414 which serves as a fulcrum. Claw sections 413a provided on tips of the paired arms 413 are capable of engaging with a pair of levers 910 provided on cap 907 of cassette 9, while the paired arms 413 are urged respectively by springs 417 so that base portions 413b may constantly be in contact with pin 415a on cam 415.

The cam 415 is rotated by driving motor 416. When the cam 415 is rotated, pin 415a presses the base portions 413b and the paired arms 413 are opened and closed accordingly.

On rotary shaft 420 of the driving motor 416, there is provided rotary disk 421, and the number of rotations of the driving motor 416 is detected by the timing with which cut-out 421a formed on the rotary disk 421 traverses photocoupler 422, to control opening and closing of the paired arms 413.

On the supporting member 412 of the cassette clinch 411, there are provided a pair of lock-releasing rods 430 which release the lock by locking mechanism 908 of cap 907. These paired lock-releasing rods 430 are supported by plate 431 on the supporting member 412 to be slidable, and solenoid 432 is linked with lock-releasing rod 430 on one side, and this lock-releasing rod 430 is linked with lock-releasing rod 430 on the other side through linking lever 433 so that both lock-releasing rods may interlock each other.

The paired lock-releasing rods 430 are constantly urged to the initial positions by springs 434, and when the supporting member 412 is brought into contact with cap 907 of cassette 9 at the position to which the cassette clinch 411 moves and solenoid 432 is moved, the paired lock-releasing rods 430 are projected and enter lock holes 909 to release the lock of lock-releasing mechanism 908.

Due to the lock release of the locking mechanism 908, the paired arms 413 are closed and claw sections 413a are engaged with a pair of levers 910 of cap 907. Under this state, the cassette clinch 411 is moved downward, storage phosphor plate 12 is drawn out of cassette 9, and supporting frame 400 is moved to be conveyed to sub-scanning section 50 while holding the storage phosphor plate 12 which is drawn out to the cassette clinch 411.

After completion of image reading for the storage phosphor plate 12, the supporting frame 400 is moved to the opposite direction to be returned to the prescribed position, then, cassette clinch 411 is moved upward and the storage phosphor plate 12 is loaded in cassette 9. In this case, when the storage phosphor plate 12 is loaded in cassette 9 without operating the paired lock-releasing rods 430 and cap 907 is closed, the lock mechanism locks the cap 907 automatically.

Image reading section 5 is built in apparatus main body 2 of radiographic image reading apparatus 1, and is arranged at the position below operation section 7. Sub-scanning section 50 provided on the image reading section 5 conveys main scanning section 51 in the sub-scanning direction.

In the sub-scanning section 50, guide shaft 500 in the direction facing the storage phosphor plate 12 and ball screw 501 are arranged to be in parallel with each other as shown in FIGS. 12, 13, 18 and 19. The guide shaft 500 is positioned at the upper part and the ball screw 501 is positioned at the lower part, and main scanning section 51 is held vertically by the guide shaft 500 and the ball screw 501 to be movable horizontally.

On the ball screw 501, there is provided direct drive motor 502, and the ball screw 501 is driven by direct drive motor 502 to rotate and thereby to move the main scanning section 51 in the sub-scanning direction.

As shown in FIG. 19, the main scanning section 51 is composed of laser beam generating section 510, polygon mirror 511, fθ lens constituting converging object 512, reflecting mirror 513 and acceptance section 514 which are solidly structured. The laser beam generating section 510 has therein a gas laser solid-state laser or a semiconductor laser as a light source. As an excitation light, the laser beam generating section 510 generates a laser beam wherein an emission intensity is forced.

A laser beam passes through an optical system and arrives at polygon mirror 511 where the laser beam is deflected, then is converged by fθ lens constituting converging object 512, and is deflected by reflecting mirror 513 in terms of optical path to be led to storage phosphor plate 12 as a scanning light for stimulating excitation. Then, image reading is conducted when stimulating emission generated by the storage phosphor plate 12 scanned by the aforesaid laser beam is accepted by the acceptance section 514. The acceptance section 514 is structured by long photomultiplier 514a and flat converging plate 514b.

A laser beam enters long photomultiplier 514a and is converted photoelectrically into electric signals corresponding to the incident light. Namely, the stimulating emission passes through flat converging plate 514b and enters long photomultiplier 514a to be converted photoelectrically. Therefore, output current corresponding to radiographic images can be obtained. The output current from the long photomultiplier 514a is converted into voltage signals by an unillustrated current/voltage converter located inside reading control section 61, and then is converted into digital image signals by A/D converter after amplified by an unillustrated amplifier. Then, digital image signals are outputted successively to main CPU 60 where various image processing including gradation processing are conducted, and the signals are stored in disk for image 63 as they are, or displayed on CRT 70.

The reading control section 61 is arranged so that various kinds of synchronization signals coming from polygon mirror 511 and detection signals for the starting position coming from a photosensor (not shown) which detects the starting position of sub-scanning may be inputted in the reading control section, and main scanning section 51 is moved from the starting position at the prescribed speed in the sub-scanning direction, while being synchronized with the main scanning made by the polygon mirror 511.

The present embodiment employs a system of incidence which is almost vertical in which an incidence angle for irradiation on storage phosphor plate 12 is 5 degrees to the surface of the storage phosphor plate 12.

The feed/load time of the radiographic image reading apparatus 1 is defined to be a period of time from the moment when cassette 9 is loaded in cassette stacker 3 to start reading up to the moment when the cassette is ready to be drawn out (175 $\mu$m reading). When the mode is a sleep mode, approximately 10 seconds are added. Further, when the maximum amount of arriving radiation on the storage phosphor plate 12 exceeds 20 mR, a maximum of 18 seconds is added.

Image reading conducted by image reading section 5 of the radiographic image reading apparatus 1 will be explained in detail as follows.

With regard to film speed on the image reading section 5, it is possible to establish the film speed in the aforesaid three steps for each region.

Namely, the film speed includes low speed (s=equivalent to 50–200), standard speed (s=equivalent to 200–1000) and high speed (s=equivalent to 1000–5000), and values represented by s are defined to be the values wherein photomultiplier tube (PMT) sensitivities are relatively expressed under the condition of the standard of the PMT sensitivity of s=200 which corresponds to output of a digital value of 1535 for X-ray irradiation of $2.58\times10^{-7}$ C/kg (1 mR).

When a grid is arranged in the direction designated by the marks showing the upper and lower sides of a cassette, a moire can be removed, and grids respectively of 34, 40, 60 and 80 lines/cm, for example, are used as a grid to be used.

Contents of correction made by the image reading section 5 are corrections for irregularity in the main scanning direction on an apparatus (S), irregularity in the longitudinal direction (F) and irregularity in polygon (P).

As correction data, there are maintained data in two types of parameters of 87.5/175 µm for each content of correction.

On system control section 6, there are provided main CPU 60 and reading control section 61 which are structured as follows.

On the system control unit, there are conducted removal of moire and various kinds of corrections. It is used for image transmission with image control board (ICU). It is possible to display XGA-24-bit color images.

As a hard disk, system disk 62 in which system programs are stored and image disk 63 in which image information is stored are connected to the system control section 6.

With regard to image data output, it is possible to switch either priority of host computer output or priority of hard copy through establishment made by a user.

The system control section 6 conducts the following image processing by the use of a software. As gradation processing, it establishes algorithm for each region based on a radiographing menu. In an automatic mode, it conducts LUT rotation shifting through ROI setting and histogram analyses, while, in a manual mode, it conducts gradation processing through fixed LUT.

For frequency processing, it conducts frequency exaggeration. For equalization, it compresses a dynamic range of image signals. For coping with split radiographing, it copes with 2-split (longitudinal and lateral) radiographing and 4-split radiographing. As an algorithm, processing conditions are determined for the prescribed one split, and they are applied to overall images. With regard to handling of images, it handles as one image.

For confirmation of irradiation, irradiation on an arbitrary polygon is confirmed automatically. However, a front breast, a side breast, abdominal region simplicity and a front pelvis are limited to a rectangle which is in parallel with edges of an image.

With regard to judgment of an image direction, whether the head-to-tail direction of the human body is in the longitudinal direction of an image or it is in the lateral direction of an image is judged automatically. However, it is possible to apply to a front breast, an infant front breast, a breast simplicity and a front pelvis only to which the invention is not limited.

Image data which have been subjected to image processing are stored in image disk 63 representing a hard disk.

As ID information of a patient, it is possible to input a patient name through a table of the Japanese syllabary displayed on CRT 70, and types of letters to be used include, for example, katakana and Arabic figures. It is also possible to input by means of ID numbers automatically. It is further possible to input by means of Chinese characters from a patient registration terminal.

A unit of registration of ID information of a patient is a unit for inspection. For example, one inspection can cover up to 24 shots. The maximum number of inspections for which an appointment can be fixed is 100, for example.

On operation section 7, there are provided CRT 70 and touch panel 71, and on the CRT 70, there are displayed inspection appointment, operations for registration of a patient, states and setting of various parts in an apparatus and images which have been read.

As CRT 70, a 15-inch CRT (24-bit color, monochromatic 256 gradation resolution 1024×768), for example, is used and operation input is made through touch panel 71 located on the CRT 70.

Incidentally, the radiographic image reading apparatus of the present embodiment can also be used as a radiographic image erasing apparatus which erases residual images remaining on a storage phosphor plate from which radiographic images have been read by another radiographic image reading apparatus. In this case, plate holding section 4 first moves in the X-direction up to the prescribed position in the X-direction where storage phosphor plate 12 can be taken out in the vertical direction from the cassette 9 designated by instruction input from operation section 7, as shown with S1 in FIG. 20, then, as shown with S2, the plate holding section 4 takes out the storage phosphor plate 12 in the vertical direction from the cassette 9 designated by instruction input from operation section 7 at that prescribed position in the X-direction, and holds it, and next, the plate holding section 4 conveys the storage phosphor plate 12 which it is holding in the vertical direction to the cassette 9 in which the storage phosphor plate 12 has been loaded as shown with S6, sipping S3–S5, and erases residual images remaining on the storage phosphor plate 12 with erasing light from a source of erasing light of erasing section 6 while loading the storage phosphor plate 12 in the cassette 9.

Embodiment 2

A radiographic image reading apparatus in the present embodiment is an apparatus wherein the radiographic image reading apparatus in Embodiment 1 has partially been modified. Now all the points changed from the radiographic image reading apparatus in Embodiment 1 will be explained as follows.

Figure 26:
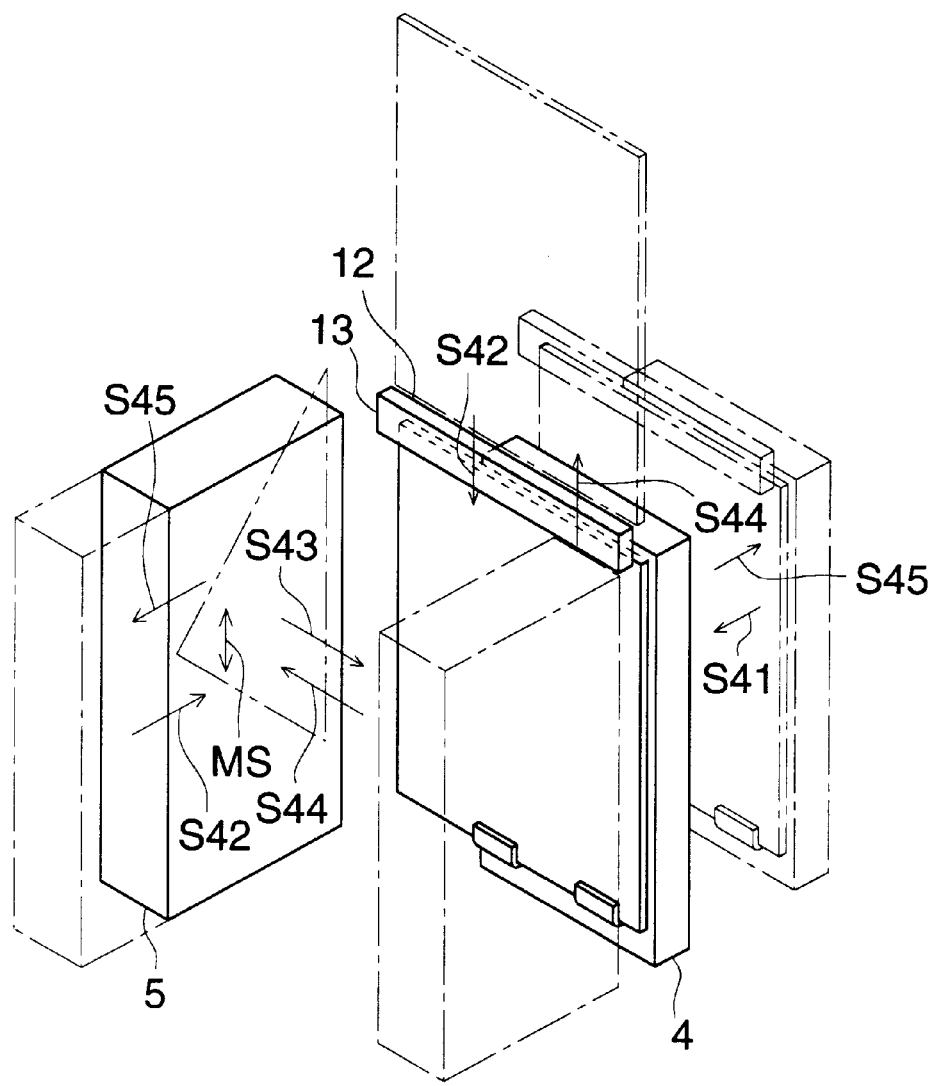
FIG. 26 is a diagram to illustrate operations of a radiographic image reading apparatus in the embodiment.

In contrast to the radiographic image reading apparatus in Embodiment 1 which is controlled as explained based on FIG. 20, in the radiographic image reading apparatus in Embodiment 2, image reading section 5 conducts main scanning MS by a laser beam in the vertical direction, and it is fixed as shown in FIG. 26, and in the first place (S41), plate holding section 4 is moved in the X-direction up to the prescribed take-out position in the X-direction where the plate holding section 4 can take out storage phosphor plate 12 from the cassette 9 designated by instruction input from operation section 7 in the vertical direction, then in the second place (S42), the storage phosphor plate 12 is taken out at the take-out position and held, and simultaneously with that, image reading section 5 is moved in the X-direction up to the prescribed position in the X-direction where the image reading section 5 can properly read images on the storage phosphor plate 12 taken out at the aforesaid position, to be stopped at that prescribed position in the X-direction, then, in the third place (S43), the image reading section 5 is moved in the Y-direction under the state where the plate holding section 4 is fixed, and thereby the image reading section 5 reads radiographic images recorded on the storage phosphor plate 12 held in the plate holding section 4, then in the fourth place (S44), the image reading section 5 is moved to its original position in the Y-direction, and simultaneously with this, the plate holding section 4 loads the storage phosphor plate 12 in the cassette at the prescribed position in the Y-direction, and erases residual images remaining on the storage phosphor plate 12, and in the fifth place (S45), the plate holding section 4 and the image reading section 5 move in the X-direction to return to home positions.

Due to the foregoing, it is possible to shorten the total time required to read radiographic images recorded on the storage phosphor plate mentioned above by moving the image reading section 5 in the X-direction while the plate holding section 4 is taking out the storage phosphor plate 12.

Embodiment 3

Figure 27:
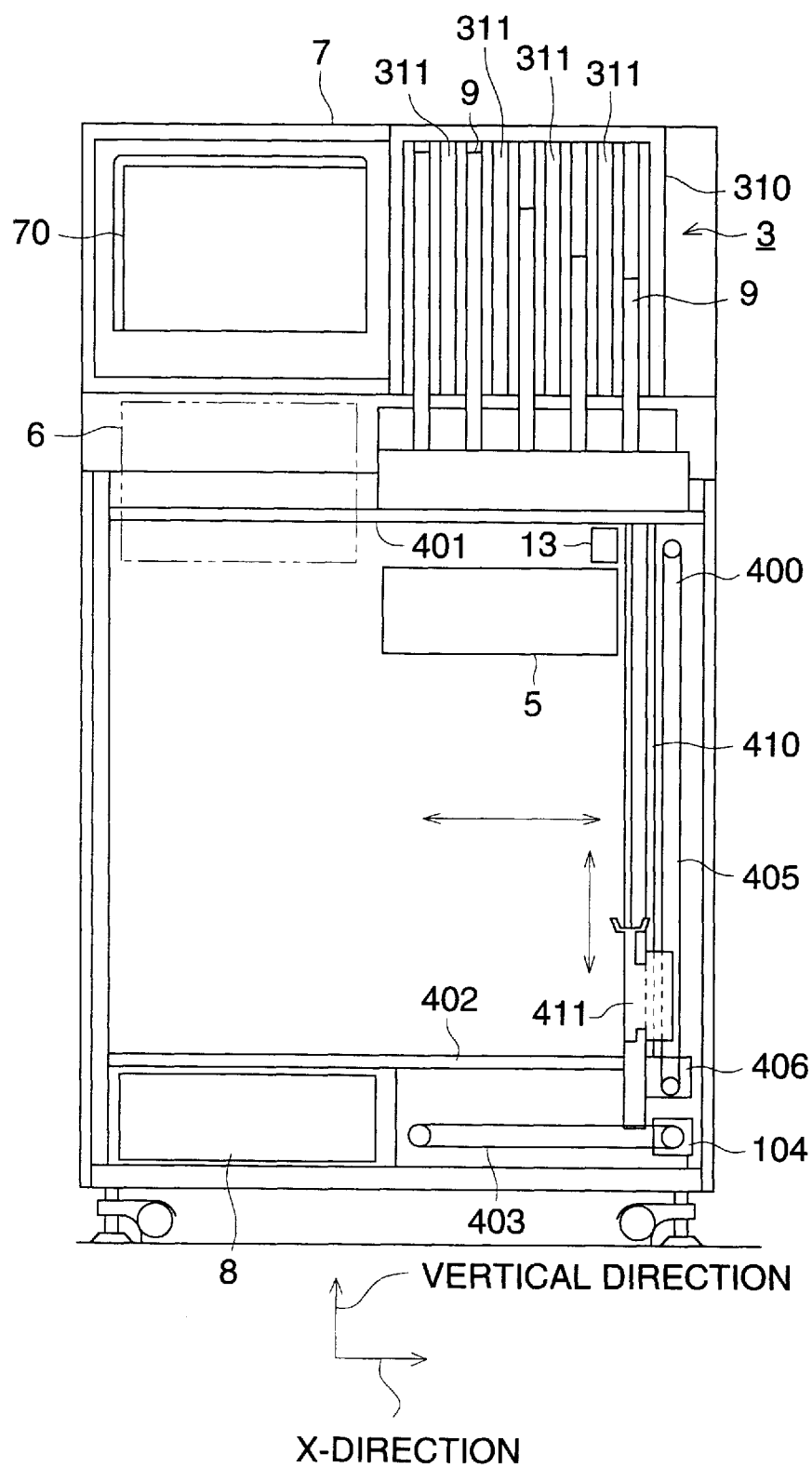
FIG. 27 is a schematic front section of a radiographic image reading apparatus in Example 3.

Embodiment 3 will be explained with reference to FIGS. 27 and 28. As shown in FIG. 27, image reading section 5 is provided on plate holding section 4 and is moved in the X-direction in the same manner as in the plate holding section 4. The image reading section 5 conducts main scanning MS by a laser beam in the Y-direction and reads radiographic images recorded on the storage phosphor plate 12 through laser scanning.

Figure 28:
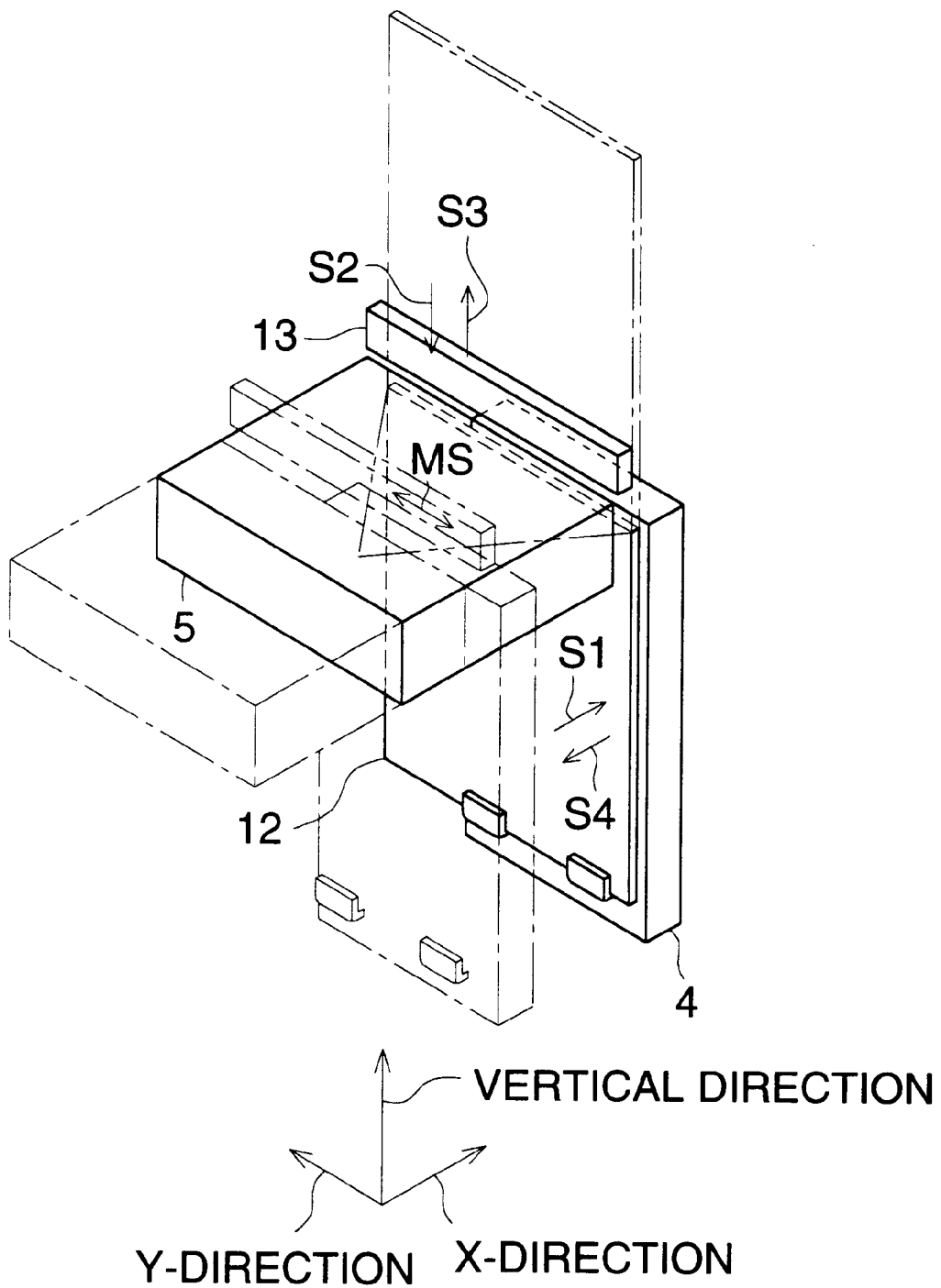
FIG. 28 is a diagram to illustrate operations of a radiographic image reading apparatus in Example 3.

Namely, as shown in FIG. 28, in the first place (S1), plate holding section 4 and image reading section 5 plus erasing section 13 both provided on the plate holding section 4 are moved to the prescribed take-out position in the X-direction where the plate holding section 4 can take out storage phosphor plate 12 almost vertically from the cassette 9 designated by instruction input coming from operation section 7.

Then, in the second place (S2), the image reading section 5 reads radiographic images recorded on the storage phosphor plate 12 which is being taken out by the plate holding section 4, when the plate holding section 4 takes out the storage phosphor plate 12 almost vertically from the cassette 9 designated by instruction input coming from operation section 7 at the prescribed take-out position in the X-direction, for sub-scanning, and when the image reading section 5 oscillates a laser beam in the Y-direction for scanning.

In the third place (S3), when the image reading section 5 finishes reading the radiographic images recorded on the storage phosphor plate 12, the plate holding section 4 causes the erasing section 13 to erase residual images remaining on the storage phosphor plate 12 while the plate holding section 4 is conveying, almost vertically, the storage phosphor plate 12 from which the radiographic images have been read by the image reading section 5 to the cassette 9 for loading the storage phosphor plate 12.

Lastly (S4), the plate holding section 4 and the image reading section 5 plus the erasing section 13 both provided on the plate holding section 4 are moved to their home positions in the X-direction.

Due to this, it is not necessary to bend the storage phosphor plate 12 for conveying it and it is therefore possible to make the floor space small, because radiographic images recorded on the storage phosphor plate 12 are read while the storage phosphor plate 12 taken out is kept to be in the vertical direction.

Since the longitudinal direction of the storage phosphor plate 12 is almost vertical, in particular, a floor space for the apparatus can be small, and further, since the oscillating direction of a laser beam for scanning is almost horizontal, the direction of scanning by a laser beam agrees with the lateral direction of the storage phosphor plate, a deflection angle of the laser beam is small, a difference of image quality between a central portion and an edge portion of an image plane is small, thereby, radiographic images recorded on the storage phosphor plate can be read properly.

Further, it is possible to read rapidly radiographic images recorded on storage phosphor plate 12, because of the structure to read radiographic images recorded on storage phosphor plate 12 by oscillating a laser beam almost in the horizontal direction for scanning while taking out the storage phosphor plate 12 almost in the vertical direction from the cassette 9 set in cassette setting section 3.

Since it is further possible to set plural cassettes 9 in the cassette setting section 3 so that storage phosphor plate 12 may be mostly in parallel with a plane formed by the vertical direction and the Y-direction to be different from others in terms of position in the X-direction, it is possible to take out the storage phosphor plate 12 from one cassette 9 and to set another cassette in another setting position simultaneously, which improves work efficiency.

In addition to the foregoing, plate holding section 4 can take out storage phosphor plate in the vertical direction from any cassette 9 set in the cassette setting section 3, and can hold it. Therefore, even when arranging so that storage phosphor plate 12 having a larger area may also be read, a larger floor space is not required, and no space is required in the periphery of the position of installation in the horizontal direction, and it hardly happens that the cassette 9 which is wrongly set is hit or something is thrown at it.

Further, since the plate holding section 4 holding storage phosphor plate 12 and the image reading section 5 have only to be moved in the X-direction and set at the prescribed relative position in the X-direction, it is technically easy to set at the prescribed relative position which is required by laser scanning.

Further, only one plate holding section 4 can load in any cassette 9 set in cassette setting section 3 the storage phosphor plate 12 which has been taken out, which makes the structure simple.

Further, since both loading the storage phosphor plate 12 in cassette 9 and erasing residual images remaining on the storage phosphor plate 12 can be conducted simultaneously, it is possible to shorten the cycle time for image reading.

Incidentally, as an example of variation of the present example, it is also possible to arrange so that the image reading section 5 reads radiographic images recorded on the storage phosphor plate 12 by oscillating a laser beam in the Y-direction for scanning, while the plate holding section 4 is conveying the storage phosphor plate 12 almost in the vertical direction when the plate holding section 4 is conveying the storage phosphor plate 12 to the cassette 9 almost in the vertical direction to load the storage phosphor plate 12, for sub-scanning, in place of that the image reading section 5 reads radiographic images recorded on the storage phosphor plate 12 which is being taken out by the plate holding section 4 when it takes out the storage phosphor plate 12 from cassette 9 almost in the vertical direction.

Due to this, it is possible to quickly load in the cassette the storage phosphor plate from which the recorded radiographic images have been read.

Embodiment 4

The present embodiment is a variation of Embodiment 3, and the present embodiment is different from Embodiment 3 on the point that reading section 5 is fixed in the present embodiment, while the reading section 5 is provided on the plate holding section 4.

Figure 29:
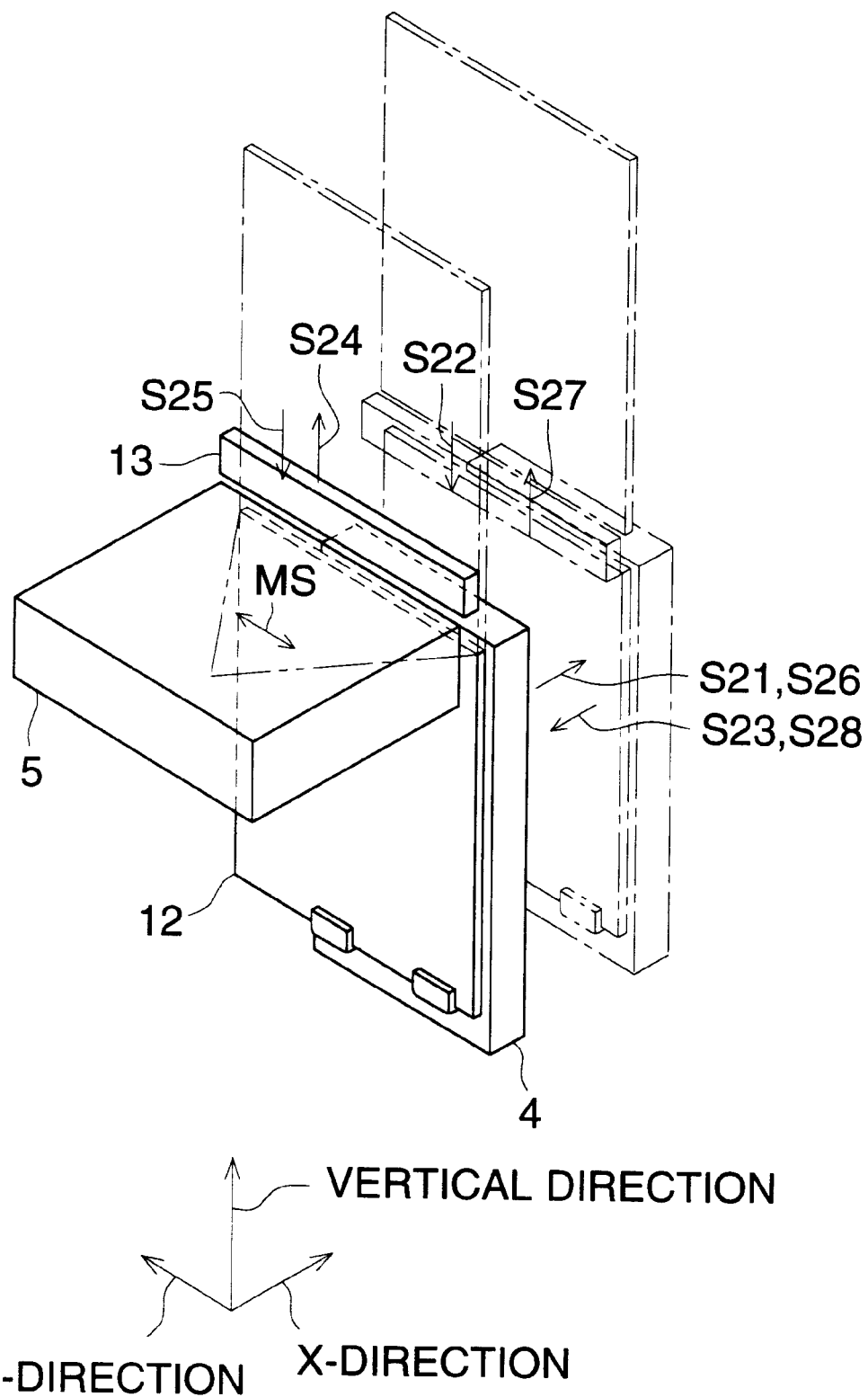
FIG. 29 is a diagram to illustrate operations of a radiographic image reading apparatus in Example 4.
Figure 30:
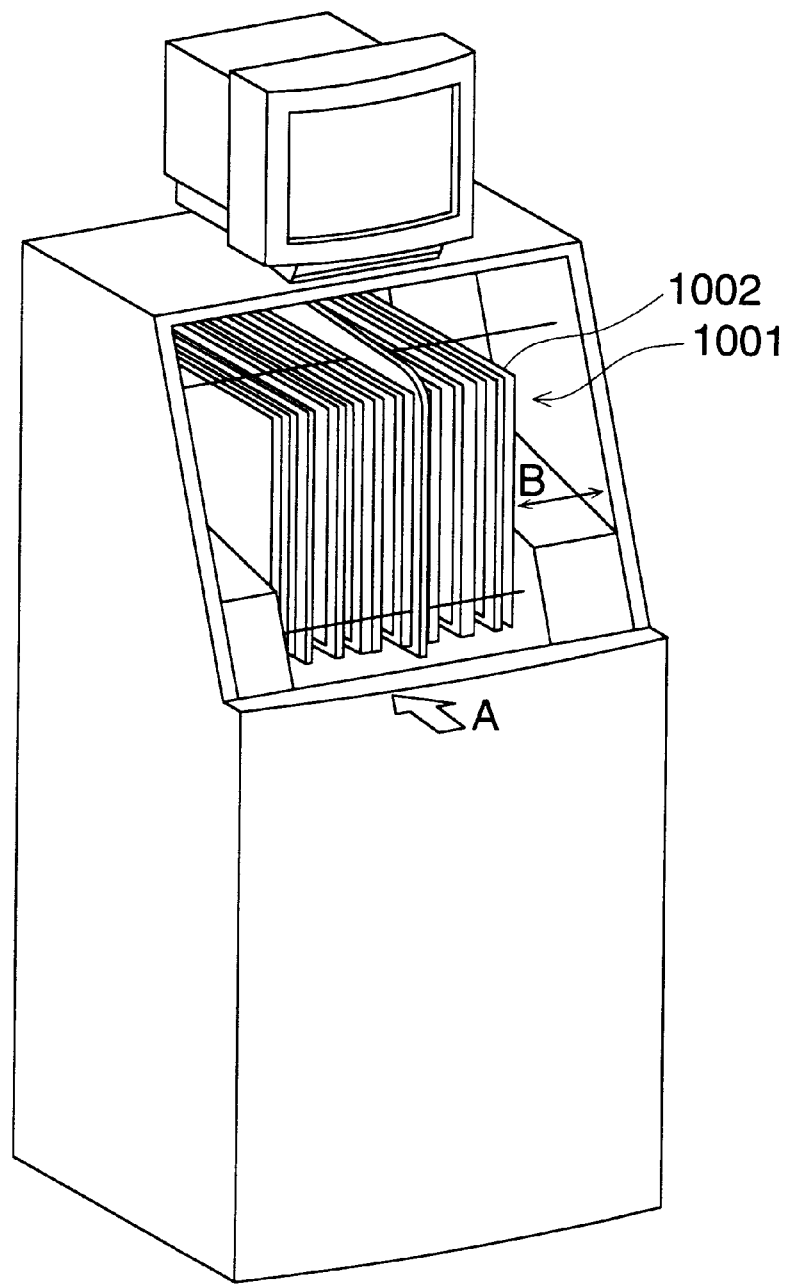
FIG. 30 is a perspective view of a conventional radiographic image reading apparatus.
Figure 31:
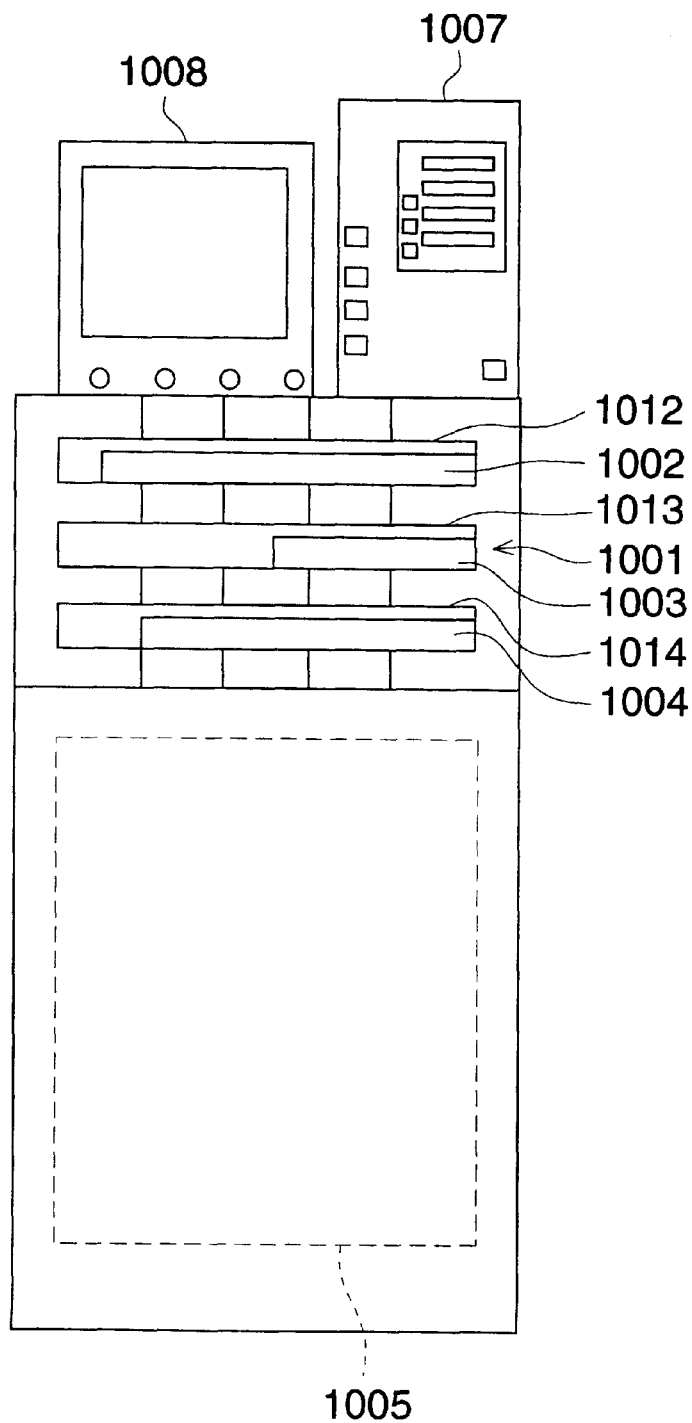
FIG. 31 is a front structure diagram of a conventional radiographic image reading apparatus.
Figure 32:
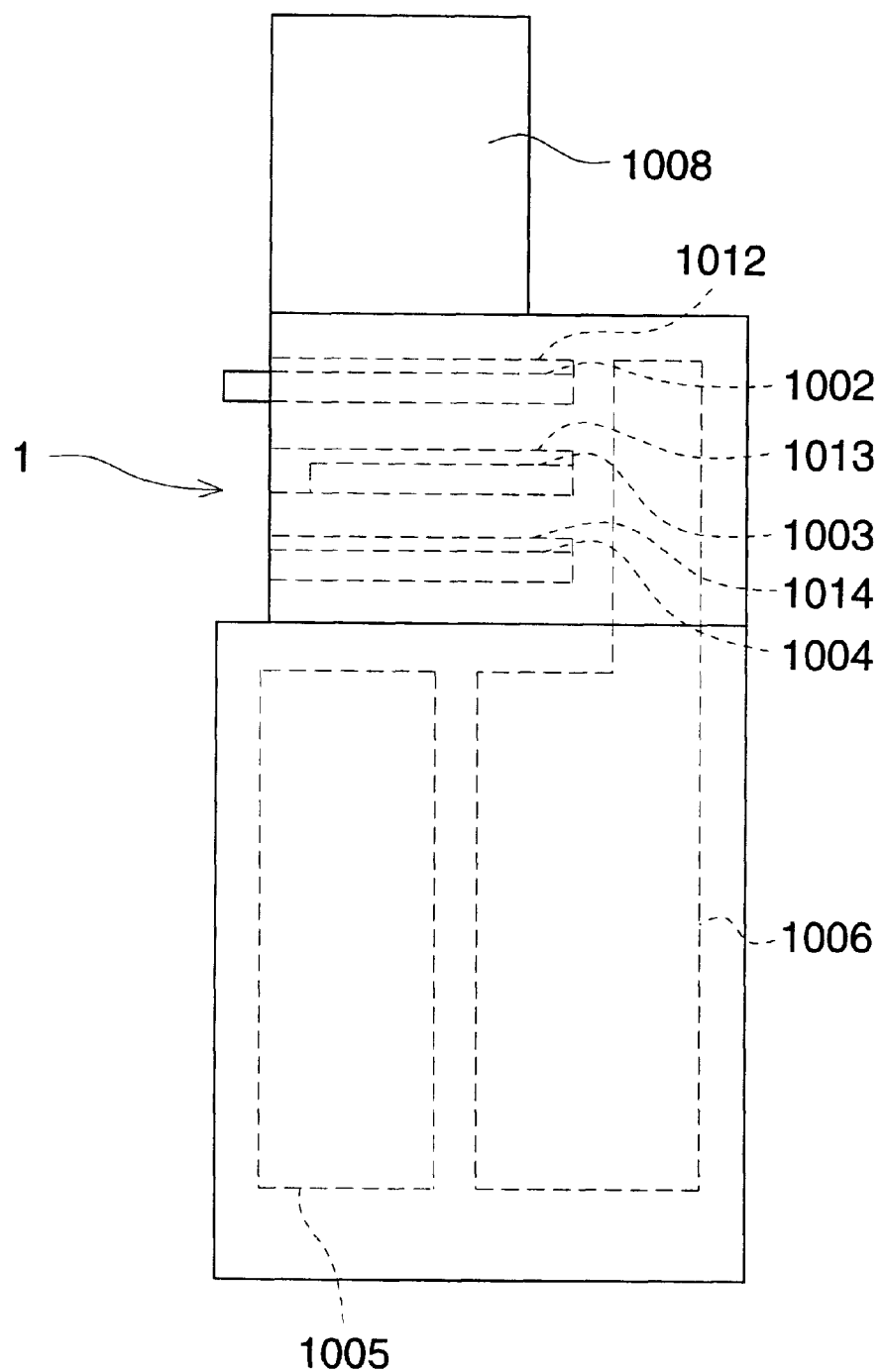
FIG. 32 is a right side structure diagram in FIG. 31.
Figure 33:
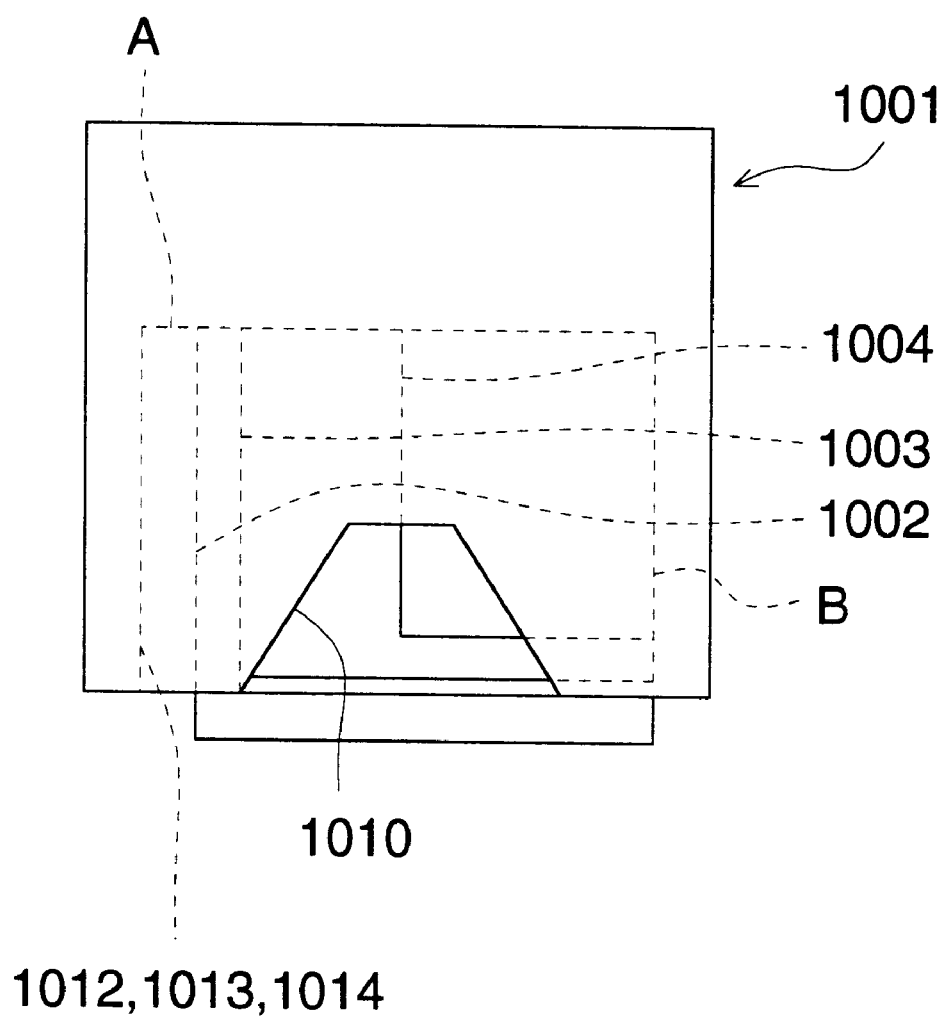
FIG. 33 is a structural diagram of a cassette stacker in FIG. 31 viewed from the upper part.

Namely, as shown in FIG. 29, in the first place (S21), plate holding section 4 and erasing section 13 which is provided on the plate holding section 4 are moved to the prescribed take-out position in the X-direction where the plate holding section 4 can take out storage phosphor plate 12 almost in the vertical direction from the cassette 9 designated by instruction input coming from operation section 7.

Then, in the second place (S22), the plate holding section 4 takes out the storage phosphor plate 12 almost in the vertical direction from the cassette 9 designated by instruction input coming from operation section 7 at the aforesaid prescribed take-out position in the X-direction, and holds it.

Then, in the third place (S23), the plate holding section 4 moves in the X-direction and stops at the prescribed reading position in the X-direction.

In the fourth place (S24), image reading section 5 reads radiographic images recorded on storage phosphor plate 12 which is being taken out by plate holding section 4 when the image reading section 5 oscillates a laser beam in the Y-direction for scanning while the storage phosphor plate 12 is subjected to sub-scanning when the plate holding section 4 holding the storage phosphor plate 12 moves the storage phosphor plate 12 in the vertical direction under the condition that the plate holding section 4 is fixed.

Then, when the image reading section 5 finishes reading the radiographic images recorded on the storage phosphor plate 12, the plate holding section 4 holding the storage phosphor plate 12 returns the storage phosphor plate 12 to its original position in the vertical direction, in the fifth place (S25).

Then, in the sixth place (S26), the plate holding section 4 moves in the X-direction and stops at the aforesaid prescribed loading position in the X-direction.

Then, in the seventh place (S27), the plate holding section 4 conveys the storage phosphor plate 12 almost in the vertical direction at the prescribed loading position in the X-direction and causes erasing section 13 to erase residual images remaining on the storage phosphor plate 12, while loading the storage phosphor plate 12 in the cassette 9.

Then, lastly (S28), the plate holding section 4 and the image reading section 5 plus the erasing section 13 both provided on the plate holding section 4 are moved to their home positions in the X-direction.

Due to this, it is not necessary to bend the storage phosphor plate for conveying it and it is therefore possible to make the floor space small, because radiographic images recorded on the storage phosphor plate are read while the storage phosphor plate taken out is kept to be in the vertical direction, and it is easy to make accurate image reading possible, because the image reading section 5 is fixed.

The invention makes it unnecessary to bend a storage phosphor plate for conveying it and makes the floor space for the apparatus small, because radiographic images recorded on the storage phosphor plate are read while the storage phosphor plate taken out is kept to be in the vertical direction.

Even when arranging so that a storage phosphor plate having a larger area may also be read, a larger floor space is not required, and no large space is required in the periphery of the position of installation in the horizontal direction, and a cassette stacker and a plate holding section can be made to be simple in terms of structure and to be inexpensive, and further, interruption processing is possible even when a conveyance path with a curved surface where a jam of a storage phosphor plate tends to happen is not provided.

It is easy to set a storage phosphor plate at the prescribed relative position which is required by laser scanning.

A cassette stacker can be made to be simple in terms of structure and to be inexpensive, and further, interruption processing is possible even when a conveyance path with a curved surface where a jam of a storage phosphor plate tends to happen is not provided. Since an image reading section is fixed in the X-direction, it is easy to make stable and accurate image reading to be possible for a long time.

Even when arranging so that a storage phosphor plate having a larger area may also be read, a larger floor space is not required, and a cassette stacker can be made to be simple in terms of structure and to be inexpensive, and it is further possible to shorten the total time required for reading radiographic images recorded on the aforesaid one storage phosphor plate, by moving the image reading section in the X-direction while the plate holding section is taking out the storage phosphor plate.

A single plate holding section can take out a storage phosphor plate from any cassette which is set in the cassette stacker, and can load the storage phosphor plate in either cassette set in the cassette stacker, which makes the structure simple.

Incidentally, interruption processing in the invention means that a storage phosphor plate is taken out of a cassette which is set newly even when some cassettes from which no image has been read are set already, and image reading is conducted from that storage phosphor plate.

What is claimed is:

1. An apparatus for reading a radiographic image, comprising:
    a stacker on which a plurality of cassettes are placed so as to stand vertically side by side;
    a holding section for holding a medium taken out from one of the cassettes; and
    a reading section that reads the radiographic image recorded on a recording surface of the medium held by the holding section so as to obtain radiographic image information from the recording surface;
        wherein the holding section is located below the stacker and shifts to a position of said one of the cassettes and takes the medium out from said one of the cassettes downward in a substantially vertical direction, and holds the medium such that the recording surface thereof is oriented substantially vertically; and
        wherein the reading section reads the radiographic image recorded on the recording surface of the medium while the holding section holds the medium such that the recording surface thereof is oriented substantially vertical.

2. The apparatus of claim 1, wherein at least one of the holding section and the reading section moves so as to come close to the other one of the holding section and the reading section after the holding section takes the medium out from said one of the cassettes.

3. The apparatus of claim 2, wherein the reading section conducts a main scanning in a vertical direction and a sub-scanning in a direction crossing at right angles with the direction of the main scanning.

4. The apparatus of claim 1, wherein the cassette has a largest surface and the plurality of cassettes are placed on the stacker such that the largest surface of the each of the plurality of cassettes is oriented substantially vertical.

5. The apparatus of claim 1, wherein the reading section conducts a main scanning in a vertical direction and a sub-scanning in a direction crossing at right angles with the direction of the main scanning.

6. The apparatus of claim 5, wherein the medium comprises a plate provided with a storageable phosphor, and the reading section comprises an irradiating device that irradiates exciting light onto the medium and a reading device that reads light emission stimulated by the exciting light.

7. The apparatus of claim 1, further comprising:

a display section provided close to the stacker in a substantially horizontal direction and that displays the radiographic image information.

8. The apparatus of claim 7, wherein the display section comprises a touch panel via which information can be inputted by touching the touch panel.

9. The apparatus of claim 8, wherein the reading section conducts a sub-scanning in a vertical direction and a main scanning in a direction crossing at right angles with the direction of the sub-scanning.

10. The apparatus of claim 1, wherein the reading section reads the radiographic image on the recording surface of the medium one of while the holding section is putting the medium into said one of the cassettes and while the holding section is taking the medium out from said one of the cassettes.

11. The apparatus of claim 10, wherein the reading section conducts a sub-scanning in a vertical direction and a main scanning in a direction crossing at right angles with the direction of the sub-scanning.

12. The apparatus of claim 10, wherein at least one of the holding section and the reading section moves so as to come close to the other one of the holding section and the reading section.

13. The apparatus of claim 1, wherein the holding section holds a portion of the medium outside an image recording area of the medium.

* * * * *